US010842944B2

(12) United States Patent
Senior

(10) Patent No.: US 10,842,944 B2
(45) Date of Patent: Nov. 24, 2020

(54) DRIVE MECHANISM FOR AN INJECTION DEVICE

(71) Applicant: Sanofi-Aventis Deutschland GMBH, Frankfurt am Main (DE)

(72) Inventor: James Alexander Senior, Warwick (GB)

(73) Assignee: Sanofi-Aventis Deustschland GMBH, Frankfurt am Main (DE)

( * ) Notice: Subject to any disclaimer, the term of this patent is extended or adjusted under 35 U.S.C. 154(b) by 144 days.

(21) Appl. No.: 16/061,624

(22) PCT Filed: Dec. 5, 2016

(86) PCT No.: PCT/EP2016/079697
§ 371 (c)(1),
(2) Date: Jun. 12, 2018

(87) PCT Pub. No.: WO2017/102395
PCT Pub. Date: Jun. 22, 2017

(65) Prior Publication Data
US 2019/0151558 A1    May 23, 2019

(30) Foreign Application Priority Data

Dec. 14, 2015    (EP) ..................... 15199711

(51) Int. Cl.
*A61M 5/31*    (2006.01)
*A61M 5/315*    (2006.01)
*A61M 5/20*    (2006.01)

(52) U.S. Cl.
CPC ...... *A61M 5/31551* (2013.01); *A61M 5/2033* (2013.01); *A61M 5/31535* (2013.01);
(Continued)

(58) Field of Classification Search
CPC .......... A61M 5/31551; A61M 5/31535; A61M 5/2033; A61M 5/31585; A61M 5/31543;
(Continued)

(56) References Cited

U.S. PATENT DOCUMENTS

2011/0077588 A1    3/2011    Hirschel et al.
2013/0289518 A1    10/2013    Butler et al.

FOREIGN PATENT DOCUMENTS

CN    101998869    3/2011
CN    102596292    7/2012
(Continued)

OTHER PUBLICATIONS

International Search Report and Written Opinion in International Application No. PCT/EP2016/079697, dated Feb. 20, 2017, 5 pages.
(Continued)

*Primary Examiner* — Amber R Stiles
(74) *Attorney, Agent, or Firm* — Fish & Richardson P.C.

(57) ABSTRACT

A drive mechanism for an injection device includes an inner body fixable inside a housing. An elongated shaft of the inner body extends in an axial direction. The shaft includes an outer thread and a blocking structure on an outer circumference. A tubular-shaped display member has an inner thread engaged with the outer thread of the inner body (20).
(Continued)

A dose member is axially displaceable between a dose setting position and a dose dispensing position relative to the display member. The dose member includes at least one blocking element displaceable, pivotable or bendable in radial direction between a blocking position and a release position and engageable with the blocking structure for inducing a radial displacement of the blocking element. In the blocking position, the blocking element axially abuts with the blocking structure and with the display member to block an axial displacement of the dose member from the dose setting position towards the dose dispensing position.

20 Claims, 7 Drawing Sheets

(52) U.S. Cl.
CPC .... *A61M 5/31543* (2013.01); *A61M 5/31585* (2013.01); *A61M 5/31541* (2013.01); *A61M 5/31575* (2013.01); *A61M 2005/3126* (2013.01); *A61M 2005/3154* (2013.01); *A61M 2205/581* (2013.01); *A61M 2205/582* (2013.01)

(58) Field of Classification Search
CPC .......... A61M 5/31541; A61M 5/31575; A61M 2005/3154; A61M 2005/3126; A61M 2205/582; A61M 2205/581
See application file for complete search history.

(56) References Cited

FOREIGN PATENT DOCUMENTS

| | | |
|---|---|---|
| CN | 103167890 | 6/2013 |
| CN | 103260674 | 8/2013 |
| CN | 103260675 | 8/2013 |
| CN | 103260676 | 8/2013 |
| CN | 104582766 | 4/2015 |
| CN | 104661696 | 5/2015 |
| CN | 105025963 | 11/2015 |
| CN | 105025964 | 11/2015 |
| EP | 2404633 | 1/2012 |
| WO | WO 2011/026928 | 3/2011 |
| WO | WO 2012/049138 | 4/2012 |
| WO | WO 2012/049139 | 4/2012 |
| WO | WO 2012/049140 | 4/2012 |
| WO | WO 2012/049141 | 4/2012 |
| WO | WO 2014/033195 | 3/2014 |
| WO | WO 2014/033197 | 3/2014 |
| WO | WO-2014033195 A1 * | 3/2014 .......... A61M 5/3157 |
| WO | WO 2014/139909 | 9/2014 |
| WO | WO 2014/139910 | 9/2014 |

OTHER PUBLICATIONS

International Preliminary Report on Patentability in International Application No. PCT/EP2016/079697, dated Jun. 19, 2018, 8 pages.

* cited by examiner

DRIVE MECHANISM FOR AN INJECTION DEVICE

The present invention relates in one aspect to a drive mechanism for an injection device, such like a pen-type injector for setting and dispensing of a dose of a medicament. In particular, the invention relates to an injection device providing a minimum dose mechanism, i.e. a dose setting and dispensing mechanism that is only operable to dispense a dose if the dose exceeds a predefined minimum threshold.

BACKGROUND AND PRIOR ART

Injection devices for setting and dispensing a single or multiple doses of a liquid medicament are as such well-known in the art. Generally, such devices have substantially a similar purpose as that of an ordinary syringe.

Injection devices, in particular pen-type injectors have to meet a number of user-specific requirements. For instance, with patient's suffering chronic diseases, such like diabetes, the patient may be physically infirm and may also have impaired vision. Suitable injection devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing including a particular cartridge holder, adapted to receive a cartridge at least partially filled with the medicament to be dispensed. Such devices further comprise a drive mechanism, usually having a displaceable piston rod which is adapted to operably engage with a piston of the cartridge. By means of the drive mechanism and its piston rod, the piston of the cartridge is displaceable in a distal direction or dispensing direction and may therefore expel a predefined amount of the medicament via a piercing assembly, which is to be releasably coupled with a distal end section of the housing of the injection device.

The medicament to be dispensed by the injection device is provided and contained in a multi-dose cartridge. Such cartridges typically comprise a vitreous barrel sealed in a distal direction by means of a pierceable seal and being further sealed in proximal direction by the piston. With reusable injection devices an empty cartridge is replaceable by a new one. In contrast to that, injection devices of disposable type are to be discarded when the medicament in the cartridge has been dispensed or used-up.

Documents WO 2014/033197 A1 and WO 2014/033195 A1 disclose disposable and reusable drug delivery devices for selecting and dispensing a number of user variable doses of a medicament. These devices comprise a housing, a cartridge holder for retaining a cartridge containing the medicament, a piston rod displaceable relative to the cartridge holder, a driver coupled to the piston rod, a display member indicating a set dose and being coupled to a housing and to the driver, and a button coupled to the display member and to the driver.

For some applications it can be advantageous to limit the minimum medicament dose that can be delivered from a device as well as the maximum dose. This may, for example, ensure that only a therapeutically effective dose can be administered. Such a functionality may be particularly relevant to combinations of drugs, where a minimum quantity of the combined drug is required to ensure sufficient delivery of one element of the combination to be therapeutically effective, whilst allowing some variation of the dose, which may be important for the other element of the combination.

In some applications it may be advantageous to offer a device which allows delivery of only one fixed dose value but also permits a 'priming' operation to be undertaken before each dose is administered.

A further application could be for a therapy in which a range of discrete, non-sequential doses of a medication may be required. For example the range of doses may be needed to satisfy the therapeutic needs of different user groups, or to allow individual users to deliver a different dose at different times of the day e.g. in the morning or in the evening.

OBJECTS OF THE INVENTION

It is therefore an object of the present invention to provide a drive mechanism for an injection device that provides a minimum dose function. It is a further object that the drive mechanism also provides a maximum dose function. It is a further aim to provide a drive mechanism that allows for a priming of the device, so that a user is able to dial and to deliver a rather small volume of medication, typically 2 international units (IU), to check whether flow occurs correctly through a needle assembly releasably attachable to a distal dispensing end of the device.

Implementation of the desired minimum and/or maximum dose function should be achievable by only modifying a limited number of existing device components. It is a further aim to individually modify minimum and maximum dose values or dose sizes by only changing a single or only a few components of the device. Hence, the minimum and/or maximum dose function of the device or its drive mechanism should be configurable by interchanging only one or a few components of the device or its drive mechanism. It is a further aim, that the improved drive mechanism is universally applicable to a large variety of drive mechanisms and injection devices. In particular, the improved drive mechanism should be equally applicable to disposable injection devices as well as to reusable injection devices. Furthermore, and in one embodiment, the drive mechanism should be operable as a so-called fixed dose mechanism exclusively operable to set and to dispense a single or multiple doses of a pre-defined, hence 'fixed' size.

SUMMARY OF THE INVENTION

In a first aspect the invention relates to a drive mechanism for an injection device. The injection device is operable to set and to dispense multiple doses of variable size of a medicament, typically by way of injection. The drive mechanism of the injection device comprises all mechanically inter engaging components that are required to exert distally directed thrust to a piston of a cartridge filled with the liquid medicament. The drive mechanism comprises an inner body that is fixable inside a housing of the injection device. The inner body at least comprises an elongated shaft that extends in an axial direction (z) and having an outer thread. The outer thread is a helical thread and comprises a well-defined constant or varying pitch in axial direction. The inner body is fixable inside the housing in a non-mobile way. Hence, the inner body is axially as well as rotationally fixable inside a tubular or cylindrically-shaped housing of the injection device. The inner body and the housing may also be integrally formed. Hence, the inner body may consist of a portion of the housing.

The drive mechanism further comprises a tubular-shaped display member having an inner thread engaged or mating with the outer thread of the inner body. The tubular-shaped display member is axially displaceable relative to the inner body, in particular relative to its elongated shaft when rotating in a helical way. Typically, the pitch and friction of the threaded engagement of the display member and the inner body is such that the display member starts to rotate when it is subject to an axial force effect relative to the inner body.

In addition, the drive mechanism comprises a dose member that is axially displaceable between a dose setting position (S) and a dose dispensing position (D) relative to the display member. The dose member may be rotatable relative to the inner body. It may be also axially displaceable relative to the inner body. Typically, the dose member is rotatable along a helical path relative to the inner body for setting or dialing of a dose. Moreover, the dose member may be axially displaceable in a non-rotative manner relative to the inner body for dispensing of a dose. The dose member and the display member may be selectively rotationally engaged, typically by means of a clutch by way of which the rotational engagement between dose member and display member is either locked or released.

In a dose setting mode the clutch is typically closed, so that a torque applied to the dose member is transferred to the display member, which upon its threaded engagement with the inner body is then displaced axially relative to the inner body in unison with the dose member. For dose dispensing the clutch between display member and dose member may be released so that the display member may rotate when returning into its initial position while the dose member is subject to a purely translational displacement. Hence, during dose dispensing the dose member may be rotationally locked to the inner body while the display member is free to rotate relative to the display body and hence relative to the dose member.

Depending on the specific embodiment of the drive mechanism either the rotating display member or the translationally displacing dose member is operably engaged with the piston rod for driving the piston rod in a distal dose dispensing direction during dose dispensing for displacing the piston of the cartridge in distal direction.

The dose member further comprises at least one blocking element which is displaceable, which is pivotable or which is deflectable or flexible in a radial direction with regard to the elongated or tubular geometry of the housing of the injection device or with regard to the elongated or tubular geometry of the inner body. The blocking element is displaceable, pivotable or deflectable between a blocking position (B) and a release position (R). The blocking element is further engageable with the blocking structure of the inner body for inducing a radial displacement of the blocking element. The dose member, in particular its blocking element is configured to engage with the blocking structure in order to displace, to pivot or to deflect in radial direction. The blocking element is particularly displaceable, pivotable or deflectable bendable radially outwardly. In the blocking position at least a portion of one blocking element is positioned or located radially outwardly compared to the release position.

When in the blocking position (B) the blocking element is engaged with the blocking structure. The blocking element further axially abuts with the display member to block an axial displacement of the dose member from the dose setting position towards the dose dispensing position. Typically, the dose member is depressible in distal direction to switch from the dose setting position towards the dose dispensing position. Since the blocking element axially abuts with the display member, which is axially constrained to the housing and in particular to the inner body thereof a displacement of the dose member in distal direction relative to the display member is effectively blocked and impeded. In this way the axial engagement of the blocking structure and the display member prevents a distally directed displacement of the dose member. Typically, the dose member and the blocking element are axially fixed relative to each other, e.g. by means of a rotationally free connection. Since a distally directed displacement of the blocking element is prevented by the axial abutment with the display member also the dose member cannot be further displaced in distal direction relative to the display member.

The drive mechanism is configured such, that application of distally directed thrust to the dose member leads to a distal displacement thereof only when the clutch between the dose member and the display member is released so that a display member is free to rotate relative to the dose member. During dose dispensing the dose member is rotatably fixed to the inner body hence to the housing. It is purely axially displaceable relative to the inner body and hence to the housing during a dose dispensing procedure. In order to release a torque transferring clutch between the dose member and the display member a small but distinct axial displacement of the dose member relative to the display member is required. As long as the blocking element is engaged with the blocking structure and axially abuts with the display member an axial displacement of the dose member relative to the display member to such a degree that the clutch therebetween would release is effectively prevented. As long as the blocking element is in axial abutment with the display member a distally directed displacement of the dose member relative to the display member is effectively impeded and the clutch between the dose member and the display member is prevented from disengaging.

A radially directed displacement, pivoting or deflection of the at least one blocking element and the resulting axial abutment with the display member is of particular benefit since any axial load, typically a distally directed load applied to the dose member is then transferable to the display member in a rather robust way. The degree of a radial displacement or radial deflection of the blocking element may be fairly small. The degree of radial displacement of the blocking element at its distal end may be as small as the thickness of the sidewall of the tubular-shaped display member or as small as the thickness of a sidewall of a tubular portion of the dose member, also denoted as dose sleeve. Due to the axial abutment between the dose member and the display member, rather large axial forces applied to the dose member can be directly transferred to the display member.

In addition, an axial load applied to the dose member may unevenly spread or split between an axial load acting on the display member and an axial load acting between the blocking element and the blocking structure of the inner body. It is of particular benefit, when an axial load distribution is somewhat unequal or inhomogeneous between the load transferring interfaces of the dose member and the display member and the interface between the dose member and the blocking structure.

By means of the axial abutment between the blocking elements of the dose member and the display member a major portion of axial thrust applied to the dose member may transfer directly to the display member and may be therefore taken away from the blocking structure of the inner body. This allows for a rather thin or fine geometric design of the interaction between the at least one blocking element and the blocking structure. Since the mutual engagement of the blocking element and the blocking structure primarily serves to generate a radial displacement of the blocking elements to arrive at an axial blocking configuration, with the display member an eventual failure or fracture of the blocking element or of the blocking structure can be effectively avoided.

Otherwise, and if the entire axial load applied to the dose member would have to be counteracted by the mechanical engagement of the blocking element with the blocking structure, failure or fracture as well as disintegration of at least one of the blocking element and the blocking structure may arise, e.g. when an excessive axial load would be applied to the dose member. By way of the direct axial engagement of the at least one blocking element with the display member such failure or fracture can be effectively avoided. This is of particular benefit in situations, where a degree of mutual engagement, e.g. an area of mutual contact between the at least one blocking element and the blocking structure is rather limited.

Typically, the blocking structure is located on the outer circumference of the elongated shaft of the inner body. The radial extension of the blocking structure typically coincides or is substantially equal to the radial extension of the elongated shaft's outer thread.

Depending on the geometric design and extension of the blocking structure dose dispensing can be effectively blocked for a predefined range of dose sizes. In this way, minimum and maximum thresholds can be defined between which dose dispensing is effectively blocked and impeded. A minimum threshold may define a maximum dose value for a priming procedure, e.g. 2 or 3 IU. A maximum threshold could define a minimum dose size, hence a dose size that has at least to be dispensed by the drive mechanism in order to ensure sufficient delivery of e.g. one element of a combined drug to obtain a desired therapeutic effect.

The geometric design of the blocking structure may also define only single dose values that may be dispensable with the drive mechanism and with the injection device. Alternatively, the mutual interaction between the blocking structure and the dose member may be configured such that only particular sequential or non-sequential set of dose values are dispensable. It is conceivable, that the drive mechanism only allows setting and subsequent dispensing of a sequential range of doses, such as 10 IU, 11 IU, 12 IU or a non-sequential range of doses, such as 10 IU, 13 IU, 23 IU, etc. Such a functionality is of particular use for administering a combination of liquid medicaments, where injection of a minimum quantity of combined medicaments is required to ensure sufficient delivery of one element of a combination to be therapeutically effective, whilst allowing some variation of the dose, which may be important for the other element of the respective combination.

For some applications it may be of particular benefit to offer an injection device that allows delivery of only one fixed dose value but that also permits a 'priming' operation to be undertaken before each dose is administered. The device and its drive mechanism may be of further use for therapies in which a range of discrete, non-sequential doses of a medicament may be required. For example a range of doses may be needed to satisfy therapeutic needs of different user groups or to allow individual users to deliver a different dose at different times of the day, e.g. morning and evening.

All these different demands can be easily fulfilled by the specific shape, design and geometry of the blocking structure on the outer circumference of the inner body. A general behavior of the drive mechanism and hence of the respective injection device is that it may be individually switched and adapted to different requirements simply by exchanging only the inner body whilst leaving all residual components of the drive mechanism unchanged. This is of particular benefit from a manufacturer's point of view. By means of modifying only one of a plurality of components of a drive mechanism the general functionality and dispensing behavior of the drive mechanism can be changed.

According to another embodiment the blocking structure comprises a blocking thread on the elongated shaft. The blocking thread may extend between convolutions of the outer thread of the inner body. In further embodiments the blocking thread is located axially offset from the outer thread of the shaft. It may be axially separated from the outer thread of the shaft. The blocking structure or blocking thread may be located at a proximal section of the elongated shaft while the outer thread may be located at a distal section of the outer shaft. The blocking thread and the outer thread may be axially non-overlapping and may be axially separated by a predefined non-zero distance. The blocking thread and the outer thread have the same pitch. Since the blocking thread and the outer thread have the same pitch and since the blocking thread and the outer thread are axially offset the blocking element remains in its blocking position during engagement with the blocking thread when the display member is subject to a helical rotation relative to the inner body during a dose dialing operation. The radial extension of the blocking structure and hence of the blocking thread may be substantially equal to the radial extension of the outer thread.

Since the blocking structure and the outer thread have the same pitch a rotation of the dose member relative to the housing and hence relative to the inner body for setting or dialing of a dose will be always possible. As long as the dose member is in a dose setting position the geometry and design of the at least one blocking element and the blocking structure is such, that the blocking element may pass along or slide along the blocking structure in accordance to the helical motion of the dose member relative to the inner body. While in the dose setting position and when dialing or setting of a dose of a particular size the at least one blocking element may be located proximally from a proximal edge of the blocking structure. The at least one blocking element may even gently touch or gently slide along a proximal edge of the blocking structure as long as the dose member is in its dose setting position. A distally directed displacement of the dose member relative to the display member for switching from the dose setting position towards the dose dispensing position then leads to an axial engagement of the at least one blocking element at the blocking structure. Upon this axial engagement, the blocking element experiences a radially outwardly directed deflection, displacement, pivoting or bending and comes into axial abutment with the display member.

Since the blocking thread and the outer thread have the same pitch the blocking functionality provided by the blocking element and the blocking structure is idle as long as the dose member is rotated relative to the inner body in accordance with the threaded engagement of inner body and display member.

According to another embodiment the blocking structure comprises at least one spiral-shaped blocking segments separated in a tangential direction by at least one gap.

Typically, there are provided at least two blocking segments between which there is provided at least one gap. When having only one spiral shaped blocking segment the gap is formed by a tangential or axial end of the respective segment. The at least one gap has a tangential size that is larger than or equal to a tangential size of the blocking element. In other words, the at least one gap intersects the blocking thread. The blocking thread may be constituted by one or by a multitude of blocking segments. In other words, the blocking segments are only portions or segments of the blocking thread that are separated by well-defined gaps. The position and size of the gaps define the dose sizes or a range of dose sizes for which the drive mechanism is switchable from a dose setting position into a dose dispensing position.

The position and size of the gaps therefore define those doses and dose ranges for which application and administering of the medicament is supported and allowable. Since the tangential or circumferential size of the at least one gap is larger than or equal to a tangential size of the at least one blocking element the blocking element is able pass through the respective gap only if the dose member is in a helical position that corresponds to a supported and allowable dose size. In such a configuration the at least one blocking element is axially aligned with or overlaps with the at least one gap but is located proximally from the blocking segment that is located tangentially adjacent to said gap. Due to the fact that a tangential size or extension of the at least one blocking element is smaller than or equal to the tangential or circumferential size of the at least one gap a smooth axial and distally directed displacement of the dose member relative to the inner body is supported and allowed.

Consequently, the dose member is then displaceable in distal direction to such a degree that the clutch between the dose member and the display member is opened and released. The drive mechanism is then switchable into a dispensing mode in which the dose member is purely axially and distally displaceable and in which the rotational coupling between the dose member and the display member is suspended thus allowing the display member to rotate in a dose decrementing sense, hence in a sense of rotation opposite to a dose incrementing dialing motion for setting of a dose. With the clutch disengaged or released the dose member and the display member may still be at least coupled in axial direction. A distally directed displacement or sliding motion of the dose member is then transferred to the display member, which due to a permanent threaded engagement with the inner body starts to rotate in the dose decrementing direction.

According to a further embodiment the dose member comprises a dose sleeve at least partially enclosing the inner body. The at least one blocking element is arranged at an inside of the dose sleeve. The dose member may also comprise a dose button, typically located at a proximal end of the drive mechanism and hence forming a proximal end of the injection device when fully assembled. Typically, the dose button and the dose sleeve are axially fixed with regard to each other. In this way, an axial abutment, hence a blocking position between the blocking element and the blocking structure can be directly transferred to the dose button. The dose sleeve provides a stiff and robust axial load transfer path between the at least one blocking element and the dose button. Any axial load applied by a user onto the dose button in the distal direction can be transferred rather homogeneously through the tubular-shaped dose sleeve. By the at least one or more blocking element or blocking elements a respective distally directed force effect can be counteracted by the display member which may be also of tubular shape.

Having the at least one blocking element arranged inside of the dose sleeve the blocking element is protected against manipulation from outside the dose member, hence from outside the dose sleeve. Moreover, by having arranged the at least one blocking element at an inside of the dose sleeve the functionality and the interaction of the blocking element with the blocking structure can be hidden. The at least one blocking element is at least partially arranged inside the dose sleeve as seen in the axial direction. The at least one blocking element is also located radially inwardly from a sidewall of the dose sleeve. It may at least partially protrude axially from an axial end of the dose sleeve. In particular, the at least one blocking element may protrude distally from a distal end of the dose sleeve.

In another embodiment the at least one blocking element comprises a distal abutment face to axially abut with a proximal abutment face of the display member. The distal abutment face of the blocking element may form a distal end of the dose member, hence of the dose sleeve. The proximal abutment face of the display member to axially engage or to axially abut with the distal abutment face of the blocking element may be located at a distal end section of the display member. The proximal abutment face may even form a proximal end face of the display member. However, also convoluted or nested arrangements of the display member and the dose member, in particular of the display member and the dose sleeve are conceivable, wherein the distal abutment face of the blocking element is located proximal from a distal end of the dose member or dose sleeve.

Alternatively or correspondingly it is conceivable that the proximal abutment face of the dose member is located distally from a proximal end of the display member. The distal abutment face and the proximal abutment face are configured to come into axial abutment as the at least one blocking element is displaced, pivoted, flexed or deflected radially outwardly as the at least one blocking element engages with the blocking structure. Otherwise and if the at least one blocking element is displaced or axially shifted through the at least one gap of the blocking structure the blocking element, hence its distal abutment face may axially pass the proximal abutment face of the display member without making contact. In an undisplaced or undeflected configuration the blocking element is located radially inward compared to the proximal abutment face of the display member. The distal abutment face and hence the blocking element may then pass by the proximal abutment face of the display member in a distal direction. Hence, there is provided at least a radial gap between the distal abutment face and the outer circumference of the inner body that is suitable to axially receive the blocking element, at least the portion of the blocking element that is provided with the distal abutment face.

In another embodiment the blocking element comprises a flexible arm section extending in an axial direction and being flexible in radial direction. Typically, a proximal end of the blocking element is rigidly attached to the dose member, in particular to the dose sleeve. The blocking element may be attached to an inside of the dose sleeve's sidewall. There may be provided a radial gap between the flexible arm section and hence between the blocking element and an inside facing sidewall portion of the dose member, hence of the dose sleeve. In this way a radially outwardly directed deflection of the at least one blocking element relative to the dose member and hence relative to the dose sleeve is supported.

In one embodiment the blocking element is integrally formed with the dose member. It is hence integrally formed with the dose sleeve. The dose sleeve as well as the majority of the residual components of the drive mechanism are configured as injection molded plastic components. In this way even a rather complex geometric structure of the dose sleeve and of all the further components can be manufactured with high precision at moderate costs and in large quantities.

In another embodiment the blocking element comprises at least one protrusion extending radially inwardly to engage with the blocking structure of the inner body. The at least one protrusion may extend radially inwardly from the flexible arm section of the blocking element. The flexible arm section may be somewhat straight in shape. It may extend in an axial direction. From the flexible arm section the at least one protrusion, e.g. in form of a cam portion extends radially inwardly to engage with the blocking structure on the outer circumference of the inner body. The at least one protrusion may comprise a rather thin or fine geometric structure. The at least one protrusion serves to induce a radially outwardly directed deflection of the at least one blocking element so that the distal abutment face thereof axially engages and axially abuts with the proximal abutment face of the display member.

Then and as soon as such a blocking position is reached almost any distally and axially directed thrust applied to the dose member and hence to the dose sleeve is directly transferable to the display member. The mutual interaction of the protrusion and the blocking structure is then outside an axial load path between the at least one blocking element and the blocking structure. Even in situations where there is only a partial tangential and axial overlap of the blocking element with the blocking structure a radial deflection of the blocking element is always attainable. Since the at least one blocking element exhibits a well-defined flexibility in the radial direction a rather small force effect acting radially outwardly to the at least one blocking element may lead to a substantive radially outwardly directed displacement or deflection thereof. A mechanical load to be transferred from the at least one protrusion to the blocking structure may be comparatively small. Thus allowing to miniaturize the at least one protrusion and the blocking structure, which is beneficial in terms of space saving.

According to another embodiment the at least one protrusion comprises a beveled edge facing in distal direction to engage with a proximal edge of the blocking structure. The proximal edge of the blocking structure may be correspondingly-shaped to the beveled edge of the at least one protrusion. It is also and alternatively conceivable that it is only the proximal edge of the blocking structure that is beveled whereas the at least one protrusion is void of a beveled edge. With both, the at least one protrusion and the proximal edge of the blocking structure having a beveled configuration a well-defined radially outwardly directed deflection or displacement of the at least one blocking element can be obtained as the blocking element and hence the dose member is displaced in distal direction relative to the inner body.

According to another embodiment the at least one protrusion of the at least one blocking element is located at a predefined proximal distance (d) from the distal abutment face. In configurations where the distal abutment face also forms a distal end of the blocking element an axial distance between the at least one protrusion and the distal abutment face leads to a certain leverage effect in terms of a radially outwardly directed deflection. Since the at least one blocking element is rather straight-shaped and extends in axial direction a radially outwardly directed deflection induced by the mutual interaction of the at least one protrusion with the blocking structure leads to a well-defined radially outwardly directed deflection of the distal abutment face, which absolute radial displacement may be even larger than the radial displacement of the protrusion.

The greater the axial distance between the at least one protrusion and the distal abutment face the more the distal abutment face will experience a radially outwardly directed displacement at a given radial height or extension of the at least one protrusion. In effect, already a rather small radial extensions of the at least one protrusion of the blocking element and/or of the blocking structure may lead to a rather large deflection of the distal abutment face of the blocking element.

According to another embodiment the at least one blocking element axially protrudes in a distal direction from a distal end of the sidewall of the dose sleeve. This allows a radially outwardly directed deflection or bending of the distal end of the blocking element and hence of the distal abutment face thereof to such a degree that the at least one blocking element even extends to such a degree that it virtually overlaps in radial direction with the sidewall of the dose sleeve. The distal abutment face or a distal end of the blocking element may even extend radially outwardly beyond the outer circumference of the dose sleeve or of the dose member. The axial protrusion of the blocking element supports and allows for a rather large radially outwardly directed deflection or bending of the at least one blocking element.

In another embodiment the dose sleeve further comprises at least one recessed portion at its inside to receive the at least one blocking element when displaced, pivoted, flexed or deflected radially outwardly. Due to the recessed portion a radial gap can be provided between the at least one blocking element and an inside of the sidewall of the dose sleeve, hence between the at least one blocking element and an inside facing sidewall portion of the recessed portion. Having a recessed portion at the inside of the dose sleeve also supports a well-defined and rather large degree of radially outwardly directed deflection or displacement of the at least one blocking element.

According to a further embodiment the dose sleeve and hence the dose member comprises several blocking elements that are equidistantly arranged at the inside of the dose sleeve. By having several blocking elements, axial load applied to the dose member can be distributed across several blocking elements each of which becomes individually in axial abutment with the display member. A mechanical load applied distally to the dose member may then be rather homogeneously transferred to the display member. The display member may in turn counteract the force acting on the dose member and hence on the dose sleeve in a distal direction.

According to another embodiment the dose member not only comprises a dose sleeve but also a dose dial, e.g. in form of a dose button that is axially fixed to the dose sleeve. Due to the axial fixing of dose dial and dose sleeve any thrust directed to the dose dial in the distal direction is immediately transferred to the dose sleeve and hence to the at least one blocking element thereof. If the at least one blocking element is in engagement or just comes into engagement with the blocking structure as distally directed thrust is applied to the dose dial the at least one blocking element is immediately flexed radially outwardly so as to get into the blocking position with the display member. Consequently a further distally directed depression of the dose dial, also acting as a dose button is effectively prevented.

The dose sleeve and the dose button may be permanently rotationally free so that a rotation of the dose sleeve has no effect on a rotation of the dose dial and vice versa. There are conceivable further configurations in which the dose dial and the dose sleeve are somewhat rigidly connected so that any axial or rotational displacement of the dose dial equally transfers to the dose sleeve and vice versa.

According to another embodiment the drive mechanism further comprises a clutch between the dose member and the display member to:
  rotatably engage the dose member and the display member when the dose member is in the dose setting position and further
  to rotatably release the dose member from the display member when the dose member is in the dose dispensing position.

By means of the clutch the drive mechanism is switchable between a dose setting or dose dialing mode and a dose dispensing mode. During dose dialing or dose setting the clutch is closed so that any rotation of the dose member and hence of the dose dial thereof equally transfers to the display member. During dose dispensing and with the clutch disengaged the display member is free to rotate back into its initial position while the dose member may be subject to a purely distally directed sliding displacement without rotation. During dose setting and in dose setting mode the dose member, the dose dial as well as the display member are subject to a helical motion with regard to the housing or with regard to the inner body. During dose dispensing the display member is subject to a dose decrementing and oppositely directed helical motion while the dose member and hence the dose dial or the dose button, typically depressed by a thumb of the user, is subject to a pure axial sliding motion. The dose dial, the drive sleeve and/or the dose member are rotatably fixed to the housing or to the inner body as the drive mechanism is switched into the dose dispensing mode.

According to a further embodiment the drive mechanism comprises a piston rod and a tubular-shaped driver, both extending in the axial direction. The piston rod typically comprises a first outer thread engaged with an inner thread of the inner body. In this way, a rotation of the piston rod in a dispensing direction leads to a distally directed advancing of the piston rod relative to the inner body and hence relative to the cartridge axially constrained inside the housing of the injection device. The piston rod may further comprise a second outer thread of opposite hand compared to the first outer thread, wherein the second outer thread is threadedly engaged with an inner thread of the driver. In this way, an axial but non-rotative displacement of the driver in the distal direction induces a rotation of the piston rod which due to the threaded engagement with the inner thread of the inner body advances in the distal direction during dose dispensing. Hence, during dose dispensing the driver is subject to a distally directed purely translational but non-rotational movement. For dose dispensing the driver is typically rotationally locked to the inner body. It may be coupled to splines in the inner body so that the driver is prevented from rotating relative to the body but is free to be axially displaced relative to the body during dose dispensing.

In a dose setting configuration the driver may be rotationally locked or rotationally coupled to the display member so as to follow the helical motion of the display member relative to the inner body. In dose setting mode, a splined engagement of driver and inner body is abrogated or released. Instead, the driver is free to rotate in accordance to a helical path that coincides with the threaded engagement of driver and piston rod so that the driver is axially displaceable in proximal direction relative to the inner body and relative to the piston rod, which during dose setting is stationary with regard to the inner body.

By means of the two threads of the piston rod of opposite hand a displacement transition ratio between the distally directed displacement of the driver and the piston rod can be implemented.

A rather large axial displacement requiring a rather low dispensing force can therefore be transferred into a rather short displacement of the piston rod with a rather large dispensing force.

According to another embodiment the dose member is permanently splined with the driver. The driver in turn is selectively rotationally lockable to the inner body by displacing the dose member into the dose dispensing position. When the dose member is in dose setting position the driver is no longer rotationally locked to the body but is free to rotate relative to the body, e.g. by means of a ratchet or detent engagement by way of which the rotation of the driver relative to the body produces an audible and tactile click sound thereby indicating to the user, that subsequent discrete steps of dose setting actually take place.

The driver and the display member may be axially engaged either directly or indirectly via axial engagement of the dose member with both, the driver and with the display member.

The clutch between display member and dose member is released when the dose member is switched or depressed into its dispensing position. In the dispensing position or dispensing configuration the dose member is axially distally displaced in a non-rotative way relative to the inner body. The dose member, the driver and the display member remain axially engaged. A depression of the dose member or exertion of a distally directed dispensing force onto the dose member therefore leads to a distally directed helical twisting motion of the display member together with a distally directed translation of the driver to induce a driving torque to the piston rod.

When implemented as a mechanism for a disposable injection device the dose member and the driver may be permanently rotationally locked. For instance, the dose member and driver may be splined together so that the dose member is prevented from rotating during dose dispensing by the driver being rotationally locked to the inner body.

In another aspect the invention further relates to an injection device for setting and dispensing of a dose of a medicament. The injection device is typically configured as a pen-type injector. It comprises an elongated housing to accommodate a drive mechanism as described above and a cartridge arranged inside the housing and filled with a liquid medicament. The cartridge is typically located and accommodated within a cartridge holder forming a distal portion of the housing of the injection device. When the injection device is implemented as a disposable device the cartridge holder and the proximal housing component are typically permanently interconnected. This connection is of non-disintegrable type. Separation of the proximal housing and the cartridge holder requires destruction or breaking of one of these components. When implemented as a reusable device the cartridge holder is releasably connected with the proximal housing part so as to provide access to the cartridge for cartridge replacement as well as to enable a reset operation of the drive mechanism.

In the present context, the distal direction points in the direction of the dispensing end of the device, where, preferably a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the injection device, which is directly operable by a user to be rotated for setting of a dose and which is operable to be depressed in distal direction for dispensing of a dose.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the abovementioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(w-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ille-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

BRIEF DESCRIPTION OF THE DRAWINGS

In the following, embodiments of the drive mechanism and the injection device are described in detail by making reference to the drawings, in which.

DETAILED DESCRIPTION

Figure 1:
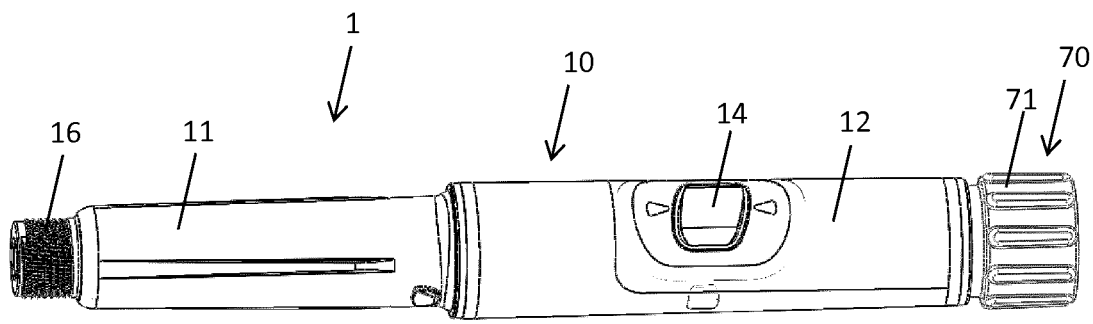
FIG. 1 shows a perspective outer view of the injection device.
Figure 2:
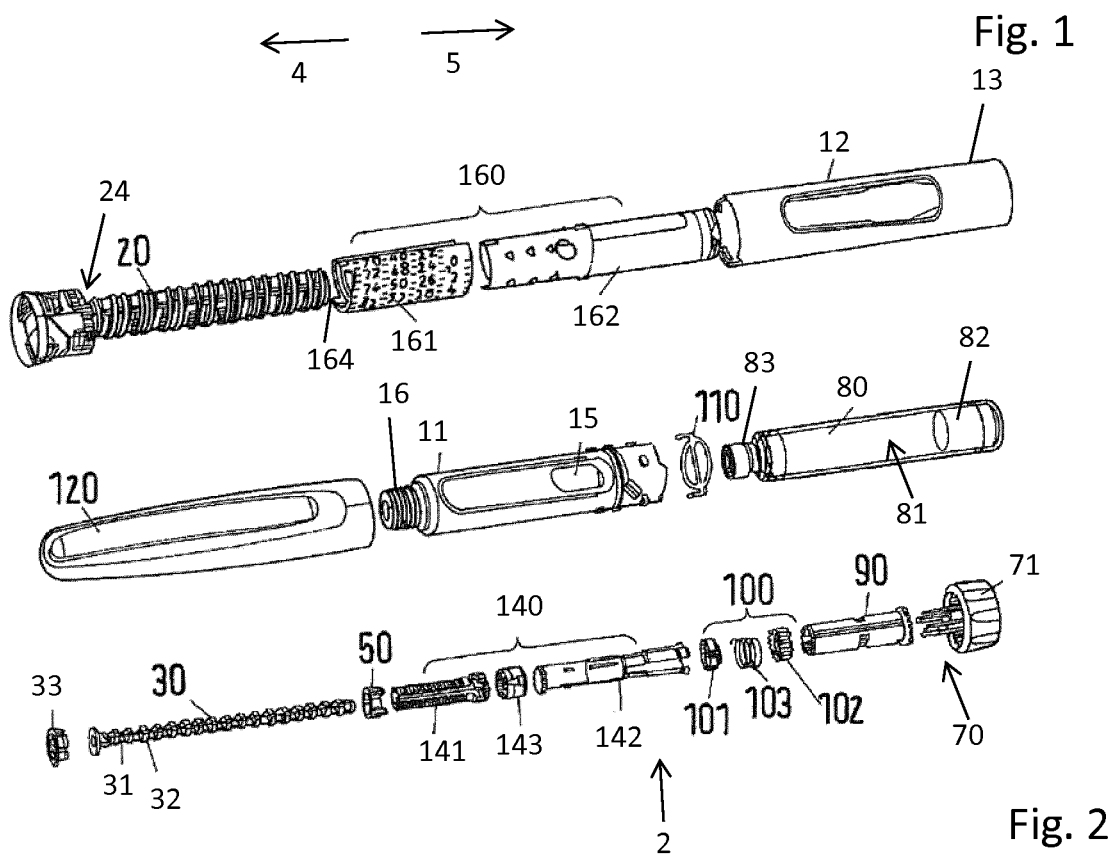
FIG. 2 shows an exploded view of an embodiment of the injection device.
Figure 3:
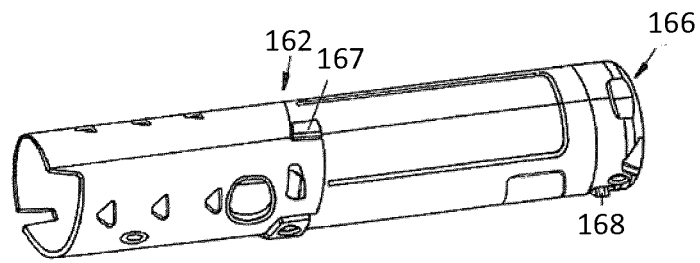
FIG. 3 shows a dial sleeve of the display member according to FIG. 2.

FIG. 1 shows a drug delivery device 1 in the form of an injection pen. The device has a distal end, shown as left end in FIG. 1 and a proximal end located at the right hand side FIG. 1. The components or parts of the drug delivery device 1 and its drive mechanism 2 are shown in FIG. 2 in more detail but without showing the blocking element 174 or blocking structure 40 and without showing the dose sleeve 72. The drug delivery device 1 comprises an outer housing part 12, a cartridge holder 11, an inner body 20, a piston rod 30, a driver 140, a last dose nut 50, a display member 160, a dose member 70, a cartridge 80 and a cap 120, i.e. in total nine separate component parts. Even though not shown in FIG. 2, a needle arrangement comprising a needle hub and a needle cover may be provided as additional components, which can be exchanged. The general concept and structure of the drive mechanism as shown in FIGS. 2 to 18 is similar and partially identical to a re-usable mechanism disclosed in WO 2014/033195 A1, which is incorporated herein by reference. The drive mechanism may be also implemented as a disposable drive mechanism being void of a reset function as disclosed in WO 2014/033197 A1, which is also incorporated herein by reference.

The cartridge 80 includes a pre-filled, necked-down cartridge reservoir 81, which may be typically made of glass. A rubber type bung 82 or stopper is located at the proximal end of the cartridge reservoir 81, and a pierceable rubber seal (not shown) is located at the other, distal, end. A crimped annular metal cap 83 is used to hold the rubber seal in place. The cartridge 80 is provided within the cartridge holder 11 with bearing 33 of piston rod 30 abutting bung 82. FIG. 2 shows the cap 120 detached from the distal end of the device 1, thus giving access to the cartridge holder 11. The cap 120 may be releasably snapped onto the outer housing 10 and can be taken off for use of the device 1.

The outer housing part 12 is a generally tubular element forming a proximal part of the housing 10 of the device 1. A cartridge holder 11 for receiving the cartridge 80 and forming a distal part of the housing 10 is detachably connectable to the proximal housing part 12, which forms an outer body. In one embodiment, the outer housing is transparent, with the outer body 12 being provided with an opaque layer 13. The opaque layer 13 covers most of the outer body 12 with the exception of a transparent window 14. Apertures 15 may be provided in the cartridge holder 11. Further, at its distal end the cartridge holder 11 has a thread 16 or the like for attaching the needle hub 2.

Figure 14:
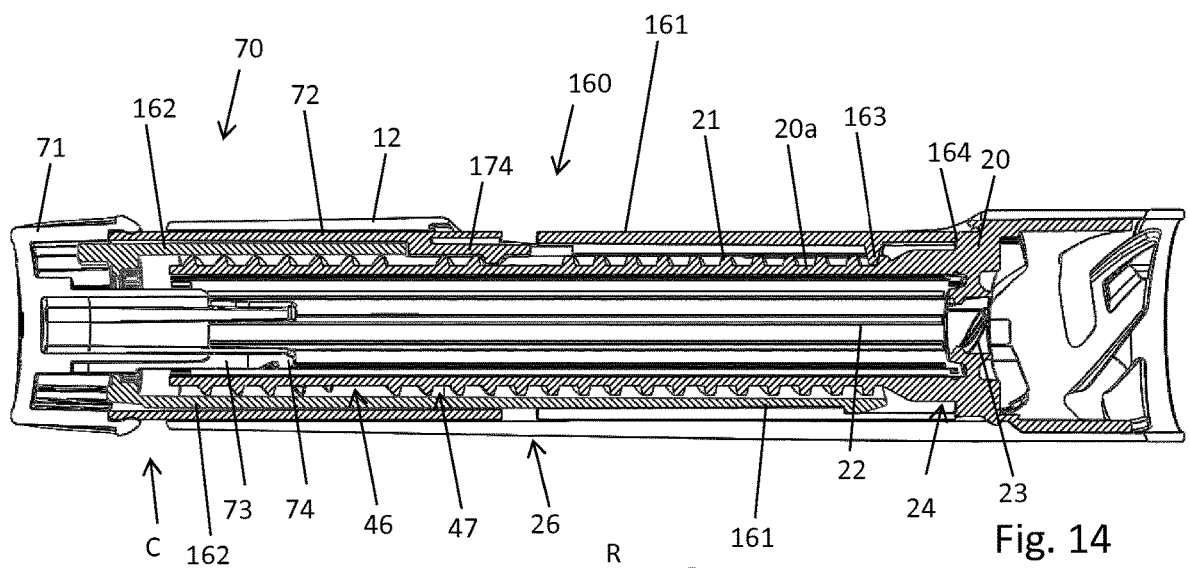
FIG. 14 shows a longitudinal cross section of the housing, the inner body, the display member and the dose member.

The inner body 20 is a generally tubular element having different diameter regions. The inner body 20 is received in the outer body 12 and permanently fixed therein to prevent any relative movement of the inner body 20 with respect to the outer body 12. An external thread 21 is provided on the outer surface of a shaft portion 20a of the inner body 20. Further, splines 22 are provided on the inner surface of the inner body 20 which are shown in FIG. 14. The inner body 20 has near its distal end an inner thread 23.

The piston rod 30 is an elongated element having two external threads 31, 32 with opposite hand which overlap each other. One of these threads 31 engages the inner thread 23 of the inner body 20. A disk-like bearing 33 is provided at the distal end of the piston rod 30. As shown in FIG. 2, the bearing 33 may be attached to the piston rod 30 as a one-piece component via a predetermined breaking point. This allows that the bearing 33 is attached to the piston rod 30 such that the bearing 33 remains seated on the distal end of the piston rod 30 to allow relative rotation between the bearing 33 and the piston rod 30.

In this embodiment, the driver 140 is a generally tubular element having in the embodiment shown in the Figures three components 141, 142, 143 which are depicted in FIGS. 2, 5, 6 and 8 in more detail. The driver 140 comprises a distal drive sleeve 141, a proximal drive sleeve 142 and a coupler 143. The distal drive sleeve 141 comprises an inner thread 142a that engages with the piston rod thread 32 to drive the piston rod 30 through the inner body 20 during dose delivery. The distal drive sleeve 141 is also permanently connected to the coupler 143 which in turn is releasably engaged through reset clutch features to the proximal drive sleeve 142. The two halves of the drive sleeve 141, 142 are rotationally and axially connected during dialing and dispense, but are decoupled rotationally during device reset so that they can rotate relative to each other.

Figure 8:
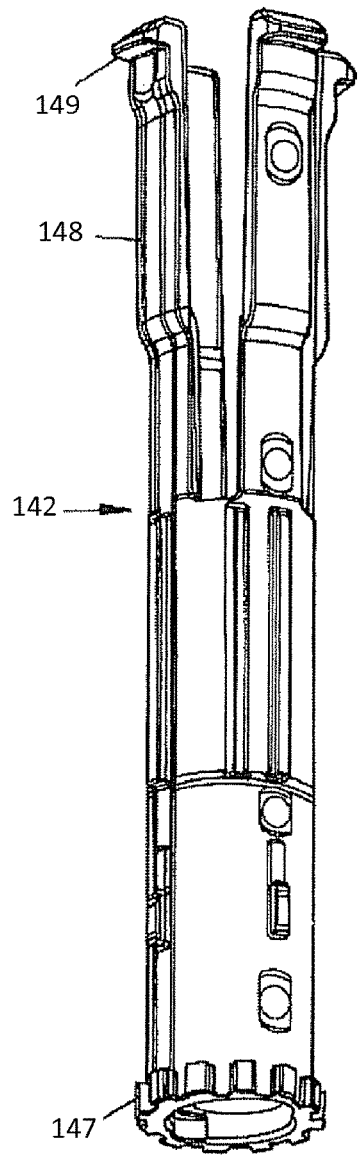
FIG. 8 shows a proximal driver part.
Figure 9:
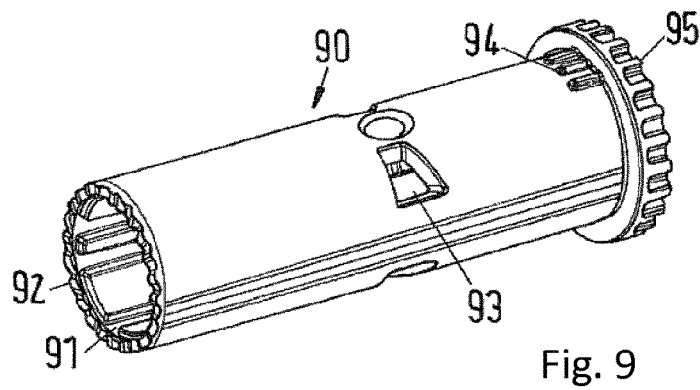
FIG. 9 shows a clutch sleeve.
Figure 10:
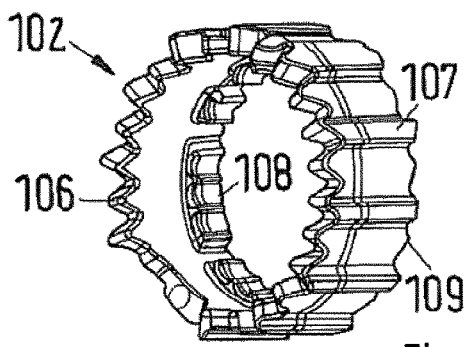
FIG. 10 is an isolated view of a proximal clicker part.
Figure 11:
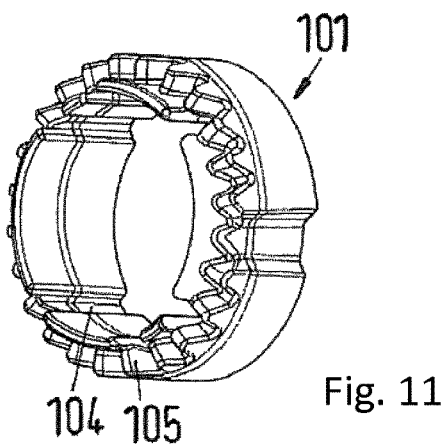
FIG. 11 is an isolated view of a distal clicker part.
Figure 12:
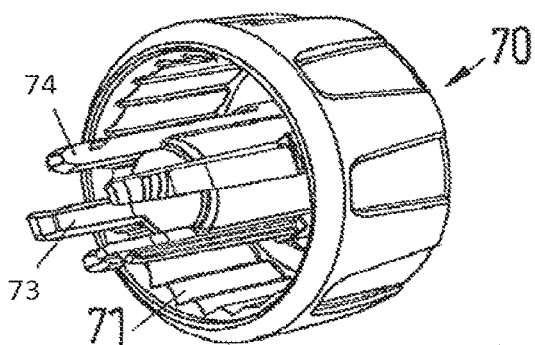
FIG. 12 shows a proximal part of the dose member.
Figure 13:
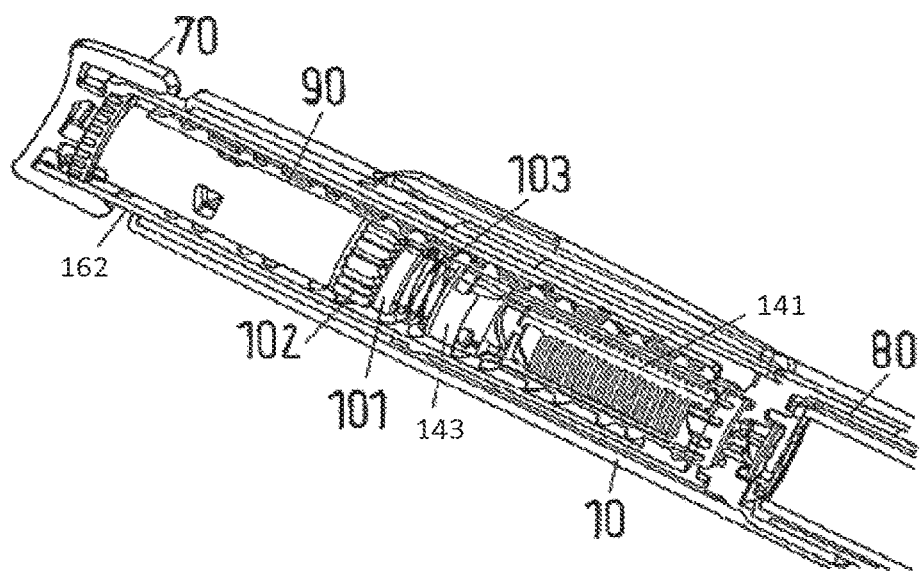
FIG. 13 is a partially cut view through the drive mechanism when assembled in the injection device.

The proximal drive sleeve 142 shown in FIG. 8 supports components of a clicker 100 and sleeve shaped clutch sleeve 90 and transfers rotational movement from the dose member 70 to the coupler 143 and distal drive sleeve 141. Teeth features 147 located at the distal end of proximal drive sleeve 142 engage with the reset clutch features on the coupler 143 to connect both halves of the drive sleeve during dialing and dispense. During reset these teeth 147 disengage.

Several splines are provided on the outer surface of proximal drive sleeve 142 engaging with a distal clicker part 101, preventing relative rotation during dialing and dispense. Further splines, which are located in the middle region of proximal drive sleeve 142, engage with the clutch sleeve 90 component. They may be arranged to be non-rotationally symmetric so that the various clicker components cannot be assembled accidentally upside down.

The proximal portion of proximal drive sleeve 142 has four arms or fingers 148. A hook-like bearing surface 149 exists on the underside of flange segments on the end of the flexible fingers 148 as seen in FIG. 8. The flexible fingers 148 are separated with gaps or slots that make space for the dose member 70 to snap to the clutch sleeve 90 and also enable these fingers to flex inwards during assembly of the proximal drive sleeve 142 to a dial sleeve 162. After assembly the hooks 149 retain the proximal drive sleeve 142 relative to the dial sleeve 162 under the reaction force from the spring 103.

During dispense the dose member 70 depresses the spring 103 via the clutch sleeve 90 and the clicker components and this spring 103 is reacted through the coupler 143 to the proximal drive sleeve 142 which then through bearing surfaces 149 applies axial load to the dial sleeve 162. This axial load drives the dial sleeve 162 and hence a number sleeve 161 along the helical thread of the inner body 20, back into the body of the device, until the zero dose stop faces 164 on the number sleeve 161 contact the inner body 20.

Figure 6:
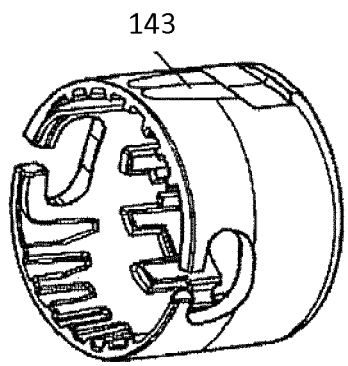
FIG. 6 shows an isolated view of a coupler.
Figure 7:
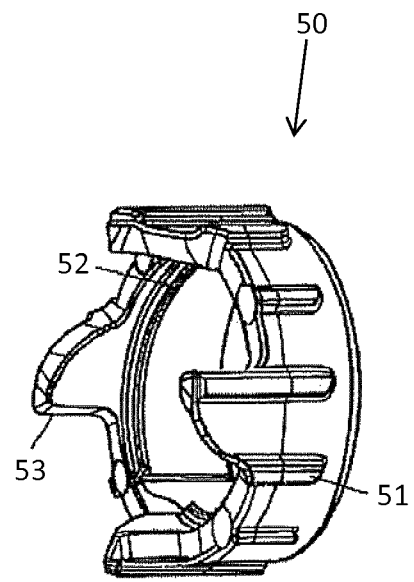
FIG. 7 shows an isolated view a last dose nut.

The coupler 143 shown in FIG. 6 rotationally couples the two halves of the drive sleeve 140 together during dialing and dispense, whilst allowing them to de-couple during reset. The coupler 143 has to also transfer the last dose stop load from the proximal drive sleeve 142 to the distal drive sleeve 141. Two sets of teeth are provided in the coupler 143 for engaging teeth 146 and teeth 147, respectively. The coupler 143 is snapped onto distal drive sleeve 141 allowing limited relative axial movement with respect to the proximal drive sleeve 142.

The last dose nut 50 is provided between the inner body 20 and the distal drive sleeve 141 of driver 140. Stop faces 53 are located on the proximal face of last dose nut 50 to limit the number of units that can be dialed if the stop faces 53 contact stops 145 of distal drive sleeve 141. The function of the last dose nut 50 is to prevent the user from dialing beyond a finite amount. This limit is based on the dispensable volume of the cartridge 80 and when reached, the user must replace the cartridge 80 and reset the device.

External ribs 51 of the last dose nut 50 engage splines 22 of inner body 20. An internal thread 52 of the nut engages the external thread 144 of distal drive sleeve 141. As an alternative, splines and ribs could be provided on the interface between the nut 50 and the driver 140 and threads could be provided on the interface between the nut 50 and the inner body 20. As a further alternative, the nut 50 may be designed as e.g. a half nut.

The display member 160 is a generally tubular element which is composed of a number sleeve 161 and dial sleeve 162 which are snapped together during assembly to axially and rotationally constrain these two components, which thus act as a single part. The dial sleeve 162 is assembled to the number sleeve 161 such that once assembled, no relative movement is allowed. The parts are made as separate components to enable both molding and assembly. Also, whereas the number sleeve 161 is preferably white to give contrast for the e.g. black dose numbers, the dial sleeve 162 color can be chosen to suit the aesthetics or perhaps to distinguish the drug type.

At the proximal end, the dial sleeve 162 has internal clutch features 165 that engage with the teeth 95 of the clutch sleeve 90 during dialing and disengage from the clutch during dispense. These clutch features 165 rotationally lock the dial sleeve 162 to the clutch sleeve 90 during dialing and when the zero and maximum dose stops are engaged. When the dose member 70 is depressed these clutch features disengage to allow the clutch sleeve 90 to move axially whilst the dial sleeve 162 and number sleeve 161 spin back to the zero unit start position.

Figure 4:
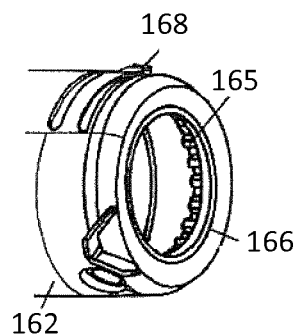
FIG. 4 shows a proximal end of the display member according to FIG. 2.
Figure 5:
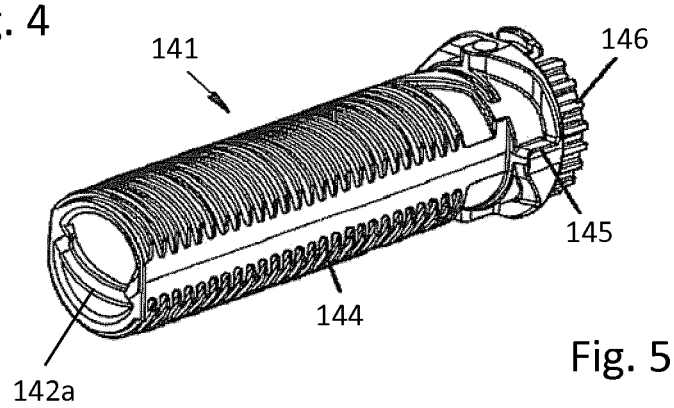
FIG. 5 is an isolated view of a distal driver part according to FIG. 2.

The dial sleeve 162 rotates out during dialing through its engagement with the clutch sleeve 90 and number sleeve 161, and rotates back in during dispense under the axial force applied by the proximal drive sleeve 142 to a flange-like bearing face 166 on the proximal end of the dial sleeve as shown in FIG. 4. This bearing face 166 engages with the flexible arms 148 of the proximal drive sleeve 142 during dispense. Two diametrically opposite faces 167 engage with the outer body 10 when the maximum dose has been dialed, forming the maximum dose stop faces.

A central sleeve-like portion of the dose member 70 is provided with four arms 73 having hook-like snap features 74 at their respective distal ends. The arms 73 form splined surfaces engaging with the clutch sleeve 90 to transfer torque from the dose member 70 through the clutch and proximal drive sleeve 142 to the dial sleeve 162. The snap features 74 engage apertures in the clutch sleeve 90 and are designed with angled undercut faces to maintain engagement when an axial load is applied to pull the dose member 70 out of the pen body 10. The space between arms 73 defines pockets giving clearance for the flexible arms 148 of proximal drive sleeve 142 to slide freely relative to the dose member 70 and clutch sleeve 90 when the dose member 70 is depressed and released during dose dispense.

The tubular clutch sleeve 90 is provided between the display member 160 and the dose member 70. The clutch sleeve 90 is fixed relative to and retains the dose member 70 and together they travel axially relative to the proximal drive sleeve 142 when the dose member 70 is depressed during dispense, disengaging the clutch teeth 95 from the dial sleeve clutch teeth 165. It also transfers torque from the dose member 70 to the proximal drive sleeve 142, and the dialing and zero and maximum dose stop loads from the dose member 70 via the clutch teeth to the dial sleeve 162 and number sleeve 161.

Drive sleeve splines 91 provided on an inner surface of the clutch sleeve 90 engage with the proximal drive sleeve 142. At the distal end face, clutch biasing teeth 92 are provided which mate with similar teeth 109 on the proximal clicker part 102 to ensure that in the unrestrained button out position (dialed dose) the clutch is biased in rotation to the proximal clicker part 102 under the biasing action of the clutch spring 103 thus ensuring that the dose number shown on the display member is correctly and unambiguously displayed to the user. The teeth 92 are shallow in height to prevent the proximal clicker part 102 from engaging with splines on the proximal drive sleeve 42 during dialing. Four snap apertures 93 serve to retain the snap features 74 of the dose member 70. Near its proximal end, the clutch sleeve 90 has splines 94 which at the end of dispense with the dose member 70 depressed lock to the inner body 20 to prevent the user from rotating the dose member 70 below the zero dose position.

Clutch teeth 95 engage with clutch teeth 165 of the dial sleeve 162 to rotationally couple the dose member 70 via the clutch to the number sleeve 161. During dispense the clutch sleeve 90 is moved axially and distally so as to disengage these clutch teeth 95 releasing the dial sleeve 162 to rotate back into the device whilst the clutch sleeve 90 and hence driver 140 move axially to dispense the dose.

The clicker 100 comprises a distal clicker part 101, a proximal clicker part 102 and a spring 103. The spring 103 serves to bias the dose member 70 out so that at the end of a dose the dose member 70, in particular its proximal button portion pops out, re-engaging the clutch sleeve 90 with the dial sleeve 162 ready for dialing. Further, it provides the spring force for the clicker components to provide audible and tactile feedback to the user and also provides detent positions for the number sleeve 161. In addition, it holds the two halves of the drive sleeves 141, 142 in rotational engagement during dialing and dispense, whilst allowing them to disengage during device reset.

The distal clicker part 101 is permanently splined to the proximal drive sleeve 142 and engages with the proximal clicker part 102 which in turn is splined and hence rotationally locked but axially displaceable to the inner body 20. During dialing when the driver 140 is rotated relative to the inner body 20, the two clickers 101, 102, rotate relative to each other under the compression force of the clutch spring 103. This force combined with the clicker teeth formed on the end face of each clicker provides the clicks and also the detent dialing positions During dispense the two clickers 101, 102 are pressed together under the axial dispense load applied by the user to the dose member 70 and this prevents relative rotation between the proximal drive sleeve 142 and inner body 20, driving the piston rod 30 forwards to deliver the dose. The splines 104 on the inner bore rotationally couple the distal clicker part 101 to the proximal drive sleeve 142 at all times, but allow free axial movement when the dose member 70 is depressed during dispense and when the two clickers ride over each other during dialing. The profile of the clicker teeth 105, 106 on both distal clicker part 101 and proximal clicker part 102 are identical and ride over each other under the compressive load from the spring 103 during dialing.

The proximal clicker part 102 is permanently splined to the inner body 20 by external splines 107 which prevent relative rotation with the inner body 20 during both dialing and dispense, providing clicks during dialing and locking the proximal drive sleeve 142 in rotation during dispense. Additional cylindrically shaped splines 108 also couple the proximal clicker part 102 rotationally to the proximal drive sleeve 142 when the dose member 70 is depressed, this preventing the user from dialing past 80 units with the dose member 70 depressed. Proximal clicker part 102, in addition to the primary clicker teeth 106, has clutch biasing teeth 109 on the opposite end face. These teeth mate with similar teeth 92 on the clutch sleeve 90 to ensure that in the unrestrained button out position (dialed dose) the clutch is biased in rotation by the proximal clicker part 102 under the biasing action of clutch spring 103.

The cartridge bias spring 110 is assembled as two components one after the other, the lower first and the upper second. The spring combination serves to apply an end load to the cartridge 80 so as to bias it forwards onto the end face of the ferrule in the cartridge holder 11. This ensures that when the user removes and attaches a needle, the friction between the needle cannula and septum of the cartridge 80 does not move the cartridge 80 axially relative to the cartridge holder 11. The bias spring 110 also acts to provide a force against which the user has to connect the cartridge holder 11 and this may add to the tactile feedback of a bayonet joint between cartridge holder 11 and inner body 20. The spring 100 also serves to eject the cartridge holder 11 if the cartridge holder is not correctly attached in a secure position, highlighting this error to the user.

During dose setting the dose member 70, driver 140 and display member 160 are rotationally locked together via clutch sleeve 90. Further, dose member 70, driver 140 and display member 160 are axially coupled. Thus, these three components wind out of the outer body 12 during dose setting. Clockwise rotation of the dose member 70, i.e. rotation of the dose dial 71 causes the driver 140 to rotate on a helical path and in doing so it advances along the piston rod 30 which remains fixed throughout dialing. The clicker arrangement 100 provides tactile and audible feedback to the user when dialing doses. At the maximum settable dose of 80 units, the stop features 167 engage with stop features in the housing 12 to prevent further dialing.

With the desired dose dialed, the device 1 is ready for dose dispensing. This requires pushing the proximal button portion of the dose member 70 which will result in a disengagement of the clutch sleeve 90 from dial sleeve 162 thus allowing relative rotation between the display member 160 and the dose member 70. In all conditions the driver 140 and the dose member 70 are rotationally locked together by engagement of arms 73 and fingers 148 and by splines 91 engaging corresponding splines on proximal drive sleeve 142. Thus, with the clutch sleeve 90 disengaged dose member 70 and driver 140 are rotationally locked together with the dose member 70, the driver 140 and the display member 160 still being axially coupled.

When dispensing a dose, the dose member 70 and clutch sleeve 90 are moved axially relative to the mechanism compressing the clutch spring 103. Because the proximal clicker part 102 is splined to the inner body 20 and the axial load passing through the clicker teeth 105, 106 locks the distal clicker part 101 in rotation to the proximal clicker part 102, the drive sleeve 140 and clutch sleeve 90 parts of the mechanism are rotationally locked to the inner body 20 and are thus forced to move axially whilst the dial sleeve 162 and number sleeve 161 are free to spin back into the outer housing 10. The interaction of mating threads between the piston rod 30, driver 140 and inner body 20 delivers a mechanical advantage of 2:1 between the movement of the driver and the movement of the piston rod in the embodiment shown.

In other words, axially advancing driver 40 causes the piston rod 30 to rotate which due to the threaded engagement of piston rod 30 with the inner body 20 advances the piston rod 30. During dose dispensing a dispense clicker 168, 71 is active which involves dose member 70 and display member 160. The dispense clicker provides primarily audible feedback to the user that the medicament is being dispensed.

When dispensing of a dose is complete and when the user removes the force from the end of the dose member 70, the clutch spring 103 pushes this dose member 70 proximally, re-engaging the teeth 165 and 95 between the clutch and the dial sleeve.

Resetting the device starts with removal of the cartridge holder 11 and replacing an empty cartridge with a full cartridge 80. As the cartridge holder 11 is re-attached, the bung of the new cartridge 80 contacts bearing 33, thus pushing piston rod 30 back into the housing. Initially, the piston rod 30 screws into the inner body 20, thereby axially disengaging the coupler 143 from the proximal drive sleeve 142 against the biasing force of spring 103. Once disengaged the coupler 143 is free to start rotating together with distal drive sleeve 141 and continues to do so as the cartridge holder 11 is moved axially into engagement with the inner body 20. Thus, the distal drive sleeve 141 rotates with respect to the proximal drive sleeve 142 which is still rotationally constrained in inner body 20 as clicker parts 101 and 102 are pressed together by compressed spring 103.

As the distal drive sleeve 141 rotates, last dose nut 50 is reset to its (distal) start position. Coupling the cartridge holder 11 to inner body 20 backs off the mechanism due to the bayonet structure allowing re-engagement of the proximal drive sleeve 142 with coupler 143 and thus the distal drive sleeve 141.

Figure 19:
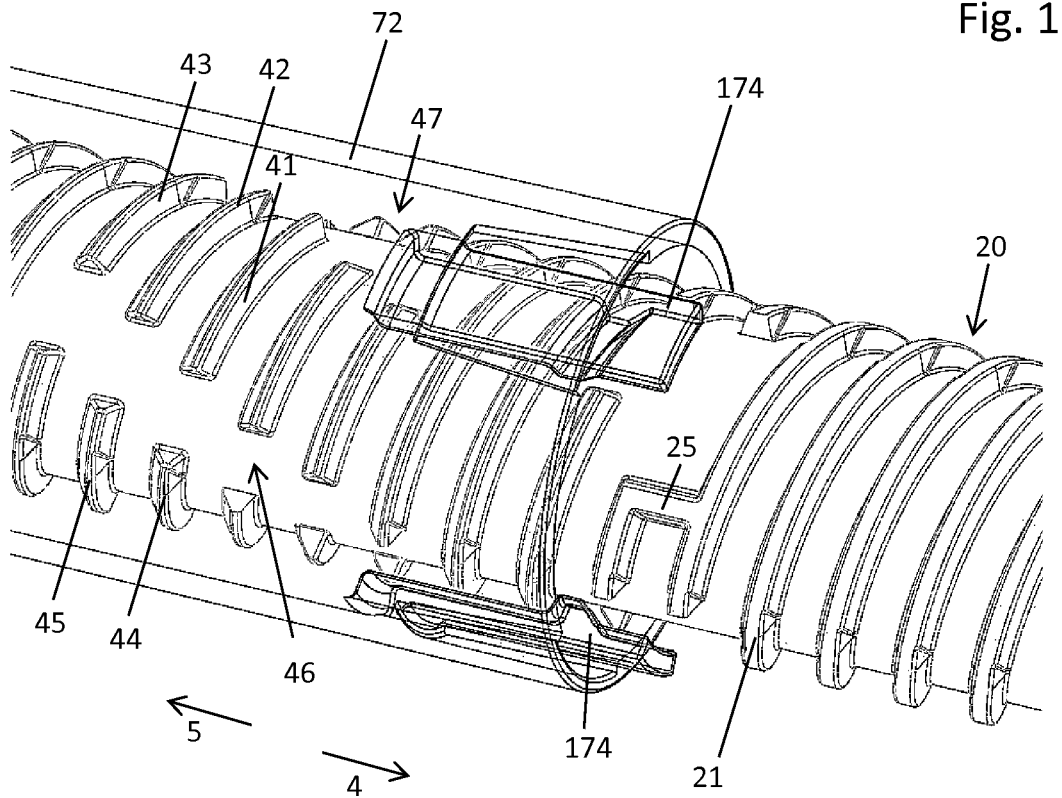

A zero unit rotational hard stop 164 is provided at a distal end of the display member 160, in particular at the distal end of its number sleeve 161. As it is apparent from FIG. 2 this stop 164 axially and/or circumferentially abuts with a stop 24 formed on the outer circumference of the inner body 20. Correspondingly and in proximal direction 5 the thread 21 is terminated by a proximal stop 25 as shown in FIG. 19 that may engage with the inner thread 163 or a stop feature provided on the inside of the number sleeve 161. A proximal or maximum dose stop may be also located on an inside of the proximal housing 12 to engage with an axially extending stop feature 167 at a proximal end of the number sleeve 161.

As it is apparent from FIGS. 14-16, 18 and 19 the inner body 20 comprises an elongated shaft 20a. Along the outer circumference of the elongated shaft 20a there is provided an outer thread 21 by way of which the inner body 20 is threadedly engaged with a radially inwardly extending thread feature or inner thread 163 of the display member 160 only shown in the cross-section of FIG. 14. In the present embodiment the outer thread 21 is located in a distal portion of the inner body 20. The elongated shaft 20a and hence the inner body 20 further comprises a blocking structure 40 on the outer circumference. In the present embodiment the blocking structure 40 is located at a proximal portion of the elongated shaft 20a. As it is apparent from FIG. 14, the outer thread 21 and the blocking structure 40 are axially separated. Hence, the outer thread 21 and the blocking structure 40 are axially non-overlapping.

Figure 18:
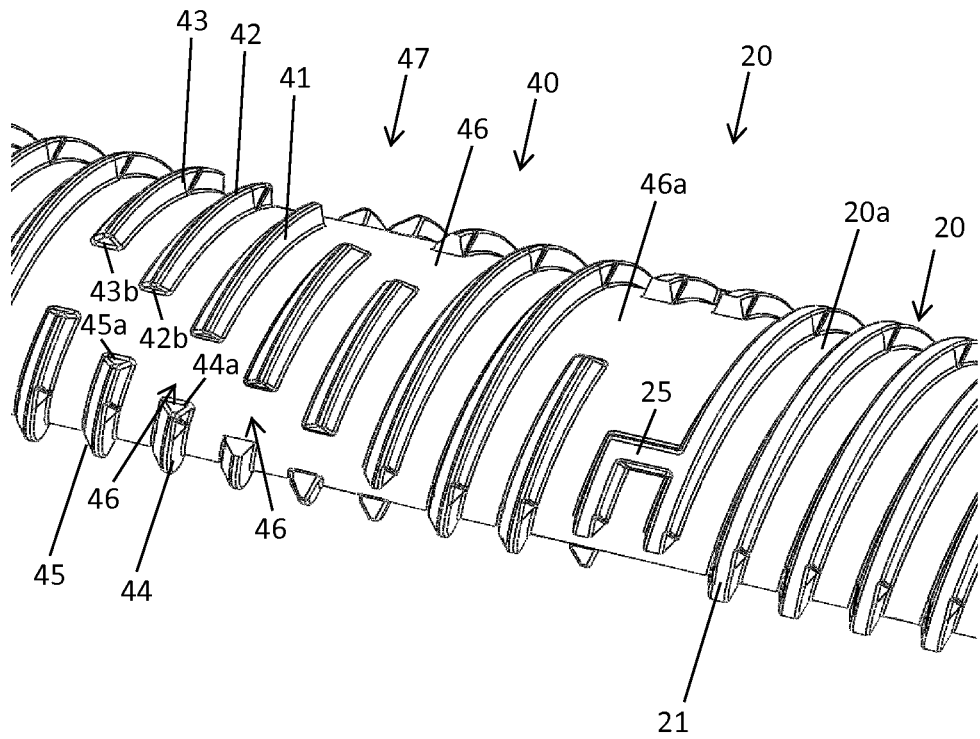
FIG. 18 is an isolated partial and perspective view of the inner body and FIG. 19 is a schematic and partially transparent view of the inner body in interaction between with the dose sleeve and the blocking elements.

The blocking structure 40 comprises or forms at least one blocking thread 47. As shown in FIGS. 18 and 19, the blocking thread 47 and the outer thread 21 have the same pitch and are of the same lead. It is in principle also possible that the axial positions of outer thread 21 and blocking structure 40 interchange so that the outer thread 21 is located at a proximal end of the elongated shaft 20a and that the blocking structure 40 is located at a distal end of the shaft 20a. It is also conceivable that the blocking structure 40 and the outer thread 21 are arranged at least partially overlapping in axial direction. Hence, the blocking structure 40 or the blocking thread 47 may be located axially in between successive convolutions of the outer thread 21 and vice versa.

The display member 160 and in particular the dial sleeve 162 thereof comprises a radially inwardly directed stepped down portion at its proximal end and is hence selectively rotationally engageable with the clutch sleeve 90 which in turn is axially fixed to the dose member 70. Via said clutch sleeve 90 and the mutually engaging teeth 95 or clutch features 165 the dose member 70 is selectively rotationally engageable with the dial sleeve 162 and hence with the display member 160. In this way a clutch C between the dose member 70 and the display member 160 is provided. As shown in FIG. 14 the dose member 70 comprises a dose button 71 or dose dial that is axially fixed to a dose sleeve 72. The dose sleeve 72 extends in axial direction and is located outside the dial sleeve 162. The dial sleeve 162 and the number sleeve 161 of the display member 160 are rigidly attached and mutually fastened. The dose sleeve 72 surrounding at least a portion of the dial sleeve 162 is displaceable in the axial direction relative to the display member 160, hence relative to the number sleeve 161 and to the dial sleeve 162 at least by a predefined axial distance.

Figure 17:
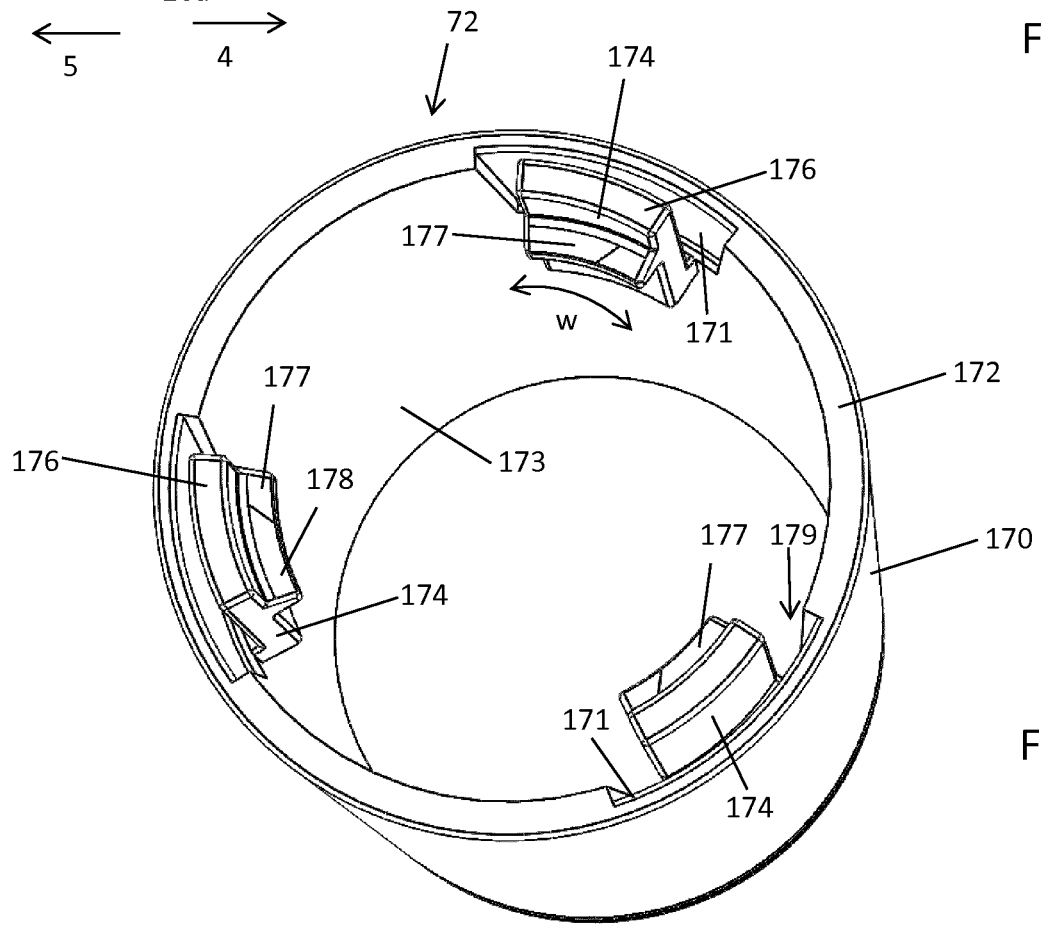
FIG. 17 is an isolated perspective illustration of the dose sleeve.

The dose sleeve 72 is rotationally fixed to the display member 160. As it is apparent from the enlarged cross-section of FIG. 15 the arrangement of number sleeve 161 and dial sleeve 162, hence the display member 160 may comprise a recess 181 to receive a fastening structure of the dose sleeve 72. Presently, the dose sleeve 72 comprises three blocking elements 174 that are located inwardly from an inside 173 of the tubular sidewall 170 of the dose sleeve 72 as shown in FIG. 17. The tangential extension or circumferential width of these blocking elements 174 matches with the tangential size or circumferential width of a recess 181 in the display member 160. Since the blocking elements 174 may be snapped into the correspondingly-shaped recesses 181 there can be formed a permanent rotational engagement and rotational coupling between the display member 160 and the dose sleeve 72.

Hence, during dose setting or dose dialing the dose sleeve 72 will rotate together with the display member 160 and due to the closed clutch C also simultaneously and in unison with the dose button 71. During dose dispensing the dose sleeve 72 rotates in the opposite direction together with the display member 160 while the dose button is rotationally fixed to the inner body 20 via the driver 140. As shown in FIG. 14, the dose button 71 is clipped over the proximal end of the dose sleeve 72 thus allowing for a relative rotation between the dose button 71 and the dose sleeve 72 but preventing any relative axial displacement between the dose button 71 and the dose sleeve 72.

Figure 15:
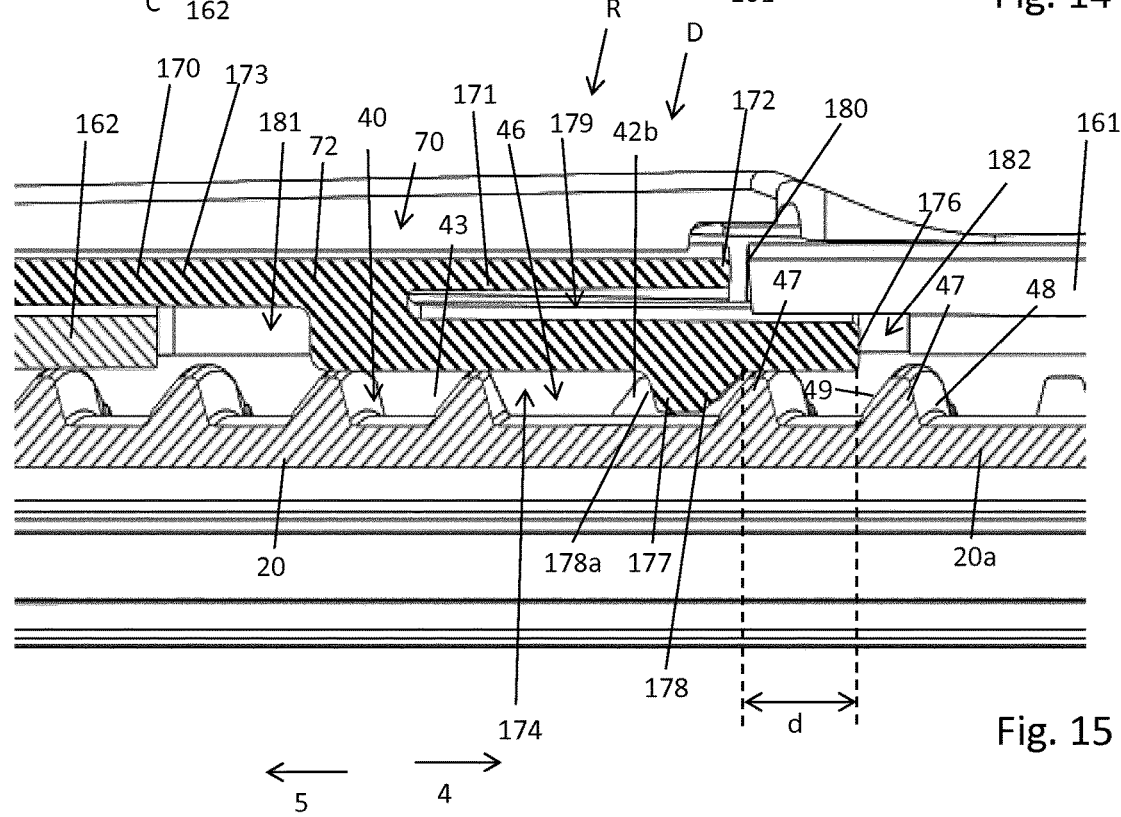
FIG. 15 is an enlarged view of FIG. 14 with the dose member in dose dispensing position.
Figure 16:
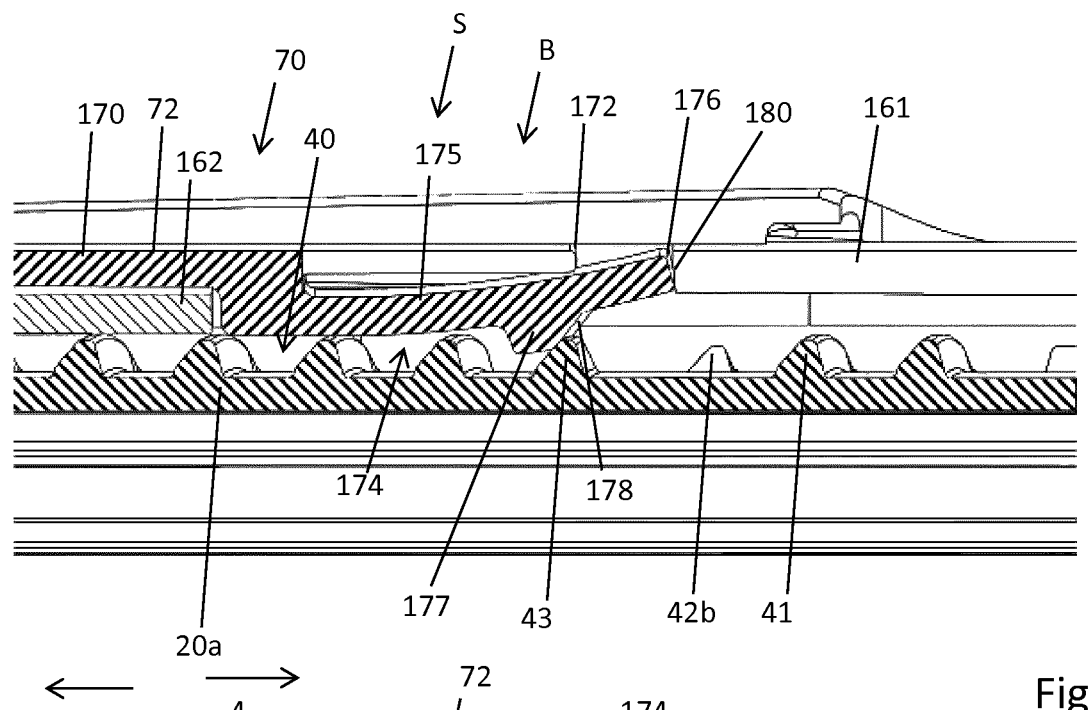
FIG. 16 is an enlarged view of FIG. 14 with the dose member in blocking position.

As it is apparent from FIGS. 15-17 the dose sleeve 72 comprises a tubular-shaped sidewall 170 having longitudinally extending recesses 171 and a distal end 172, wherein the recesses 171 comprise a radial depth that is less than the radial thickness of the sidewall 170.

The blocking elements 174 are equidistantly arranged along the inner circumference of the sidewall 170. As it is apparent from a comparison of FIGS. 15 and 16 each one of the blocking elements 174 comprises a flexible arm section 175 extending substantially in axial distal direction 4 when radially inwardly extending protrusions 177 of the blocking elements 174 are disengaged from to the blocking structure 40. In this release position R as shown in FIG. 15 the blocking elements 174 comprise an elongated and straight or even shape. At a distal end the blocking elements 174 comprise a distal abutment face 176 facing in distal direction 4. The distal end of the blocking elements 174 also protrudes from the distal end 172 of the dose sleeve 72.

The blocking elements 174, in particular their flexible arm sections 175 are radially flexible or radially deflectable to a certain degree in the radial outwardly pointing direction. The radially outwardly directed deflection as shown in FIG. 16 is delimited by the distal end 172 of the sidewall 170. Otherwise it is also conceivable, that a radially outwardly directed deflection is delimited by some other housing component of the injection device 1, such as the proximal housing part 12. Since the display member 160 as well as the dose member 70 are subject to a simultaneous proximally directed helical motion during dose dialing it is of particular benefit, when a portion of the dose sleeve 72 itself, e.g. the distal end 172 of the sidewall 170 provides a radial stop for the radially outwardly directed deflection of the blocking element 174. At its radially inwardly facing side the blocking element 174, in particular its flexible arm section 175 comprises a radially inwardly extending protrusion 177 that acts as a cam portion. The protrusion 177 comprises a beveled edge 178 facing in the distal direction. The beveled edge 178 is correspondingly-shaped to a beveled and proximal edge 49 of the blocking structure 40.

The blocking structure 40 is shown in more detail in FIG. 18. The blocking thread 47 may be interrupted or intersected by various gaps 46 extending between numerous blocking segments of which only blocking segments 41, 42, 43, 44 and 45 are denoted with reference numbers. The blocking segments 41, 42, 43, 44, 45 belong to the blocking thread 47 and constitute or form the intersected blocking thread 47. The blocking segments 41, 44 are aligned in tangential direction in accordance to the pitch of the blocking thread 47. Tangentially between a tangential end 41b of the blocking segment 41 and a tangential end 44a of the consecutive or neighboring blocking segment 44 there is provided a gap 46 having a predefined tangential or circumferential size. The tangential gap size 46 is at least as large as the tangential width of the radially inwardly extending protrusions 177 of the blocking elements 174 as shown in FIG. 17.

Similar to the blocking segments 41 and 44, two further blocking segments 42, 45, which are also separated at their tangential ends 42b, 45a by a gap 46 are located axially offset from the blocking segments 41, 44. As it is shown in FIG. 18 the gaps 46 between the blocking segments 41 and 44 and between the blocking segments 42 and 45 are somewhat tangentially or circumferentially offset. The axial as well as circumferential position and size of the gaps 46 defines discrete dose sizes or a range of a minimum and a maximum dose that can be set and dispensed by the drive mechanism 2. For dose sizes dialed by dose size In an initial or zero dose configuration as it is exemplary shown in FIG. 19 the blocking elements 174 of the dose sleeve 72 are located near a distal end of the blocking thread 47.

Each specific dose size actually set by dialing the display member 160 and the dose member 70 correlates to a well-defined position of the blocking elements 174 along the helical path of the blocking structure 40. When dialing an allowable dose size each blocking element 174 will be aligned with a gap 46 of the blocking thread 47. For dose values that must not be dispensed by the drive mechanism 2 at least one of the blocking elements 174 overlap will stay in engagement with the blocking structure 40. It will remain or get in an axial abutment with the blocking thread 47 when depressing the dose member 70 thereby blocking a dispensing procedure.

Near a distal end of the blocking structure 40 there is provided an initial gap 46a. At the end of a dose dispensing procedure the protrusions 177 of the at least one blocking element 174 will be co-aligned with this initial gap 46a so as to allow and to support a proximally directed returning of the dose member 70 towards its dose setting position S.

As a dose is dialed the dose sleeve 72 rotates in unison with the display member 160. Consequently and according to the specific geometric design of the blocking structure 40 and the blocking elements 174 the protrusions 177 are located always axially offset from the various blocking segments 41, 42, 43, 44, 45 of the blocking structure 40. As it is shown in FIG. 19 the protrusions 177 are located axially between two axially consecutive convolutions of the blocking thread 47. In typical embodiments the distally facing beveled edges 178 of the protrusions 177 are located in close proximity to the proximal edge 49 of the blocking thread 47.

They may even come into a slight contact with the blocking thread. Due to an identical pitch of the outer thread 21 and the blocking thread 47 and due to the at least unidirectional axial coupling between the display member 160 and the dose sleeve via the clutch sleeve 90 the protrusions 177 remain in a constant proximal position relative to the blocking thread 47 as the dose sleeve 72 is subject to a dose dialing rotation.

At the end of a dose setting or dose dialing procedure the protrusions 177 may either be located in a position at least partially tangentially and/or axially overlapping with a distally located blocking segment 41, 42, 43, 44 or 45 or the protrusions 177 may align with the at least one gap 46. In the latter case the dose member 70 and its blocking elements 174 is in a release position R as shown in FIG. 15. As the protrusions 177 of the blocking elements 174 are axially aligned with respective gaps 46 of the blocking structure 40 the blocking structure 40 actually allows and supports a distally directed sliding displacement of the blocking elements 174 relative to the blocking structure 40. As it is shown in FIG. 15 the protrusion 177 is axially displaceable through the gap 46 such that the protrusion 177 traverses and passes by a longitudinal end 42b of a blocking segment 42.

Prior to a distally directed depression of the dose button 71 and hence of the entire dose member 70 the protrusion 177 may be located axially between the blocking segment 42 and blocking segment 43 or between the blocking segment 44 and the blocking segment 45. In the release position R the distal end of the blocking element 174 may enter a radial gap 182 between the blocking structure 40 and an inside of the number sleeve 161 or of the display element 160 in general. Distally directed displacement of the dose member 70 may be delimited by the distal end 172 of the dose sleeve 72 getting into axial abutment with a proximal abutment face 180 of the number sleeve 161 or with a comparable proximal abutment face of the display member 160.

Due to the distally directed displacement of the dose sleeve 72 the clutch C is allowed to disengage, thereby switching the drive mechanism 2 into the dose dispensing mode D. During dose dispensing a user constantly applies distally directed pressure or thrust to the dose button 71. Under this force effect and due to the mutual interaction of dose member 70, driver 140, inner body 20 and the display member 160 the display member starts 160 to rotate in a dose decrementing direction so that dose size indicators, such as numbers printed on the outer circumference of the number sleeve 161 appear in a decreasing order in the window 14 of the proximal housing part 12. In the event that dose dispensing is interrupted, the spring 103 tends to displace the clutch sleeve 90 and the dose member 70 back into the proximal end position.

Since the blocking elements 174 were rotated during this interrupted dose dispensing procedure relative to the inner body 20, the protrusions 177 may have re-entered the blocking thread 47. Such a re-entry occurred during a depression of the dose button 71 with the dose sleeve 72 being in dose dispensing position D. Then, the respective protrusions 177 have entered a neighboring convolution of the blocking thread 47 without making contact with it. As shown in FIG. 15 a proximally facing edge 178a of the protrusion 177 is then located distally from a distal edge 48 of the blocking segment 42. In this dispensing position D a rotation of the dose sleeve 72 and hence of the blocking elements 174 relative to the inner body 20 and hence relative to the blocking structure 40 and the blocking thread 47 is possible and supported. If the user interrupts a dispensing procedure by releasing the dose member 70 the proximal edge 178a of the protrusions 177 actually engages and abuts with the distal edge 48 of the blocking thread 47. In this way the dose member is hindered from re-engaging with the display member 160. Hence, the clutch C may not re-engage and a user may not be able to change the dose initially set.

Proceeding with the partially dispensed dose is immediately possible as the user depresses the dose button 71 again in distal direction 4. The protrusion 177 did not traverse the blocking segment 42 in proximal direction 5 due to the axial abutment of the proximal edge 178a and the distal edge 48. The dose member 70 therefore remains in the dispensing position D.

In other configurations where a user selects or dials a dose that is not intended to be dispensed by the injection device 1 there will be at least a partial tangential and radial overlap of the protrusions 177 with one of the blocking segments 41, 42, 43, 44, 45 as seen in axial direction. If a user will then depresses the dose member 70 by pressing on the dose button 71 in distal direction 4 the mutually corresponding beveled edges 178, 49 of the protrusions 177 and the blocking thread 47 will lead to a radially outwardly directed deflection of at least the free end of the flexible arm section 175 of the blocking element 174. In effect and as shown in FIG. 16 the dose member 70 will then arrive at a blocking position B such that the distally facing abutment face 176 of the blocking element 174 actually abuts with the proximal abutment face 180 of the display member 160, in particular with the proximal abutment face 180 of the number sleeve 161.

In this way axial load applied to the dose member 70 via the dose button 71 and the dose sleeve 72 is directly transferred in the axial and distal direction 4 to the proximal abutment face 180 of the display member 160. The axial load applied to the dose member 70 is then somewhat unequally distributed between the display member 160 and the inner body 20. Typically, a major part of the axial load is carried and reacted by the rather solid and mechanically stable display member 160. This is of particular benefit when the protrusions 177 only partially overlap and engage with the blocking structure 40, which may be the case if a dose slightly above or slightly below an allowed dose value is actually dialed. If the entire axial load applied to the dose member 70 would have to be reacted exclusively by the inner body 20 so that the entire axial load would traverse through the axial abutment of the protrusion 177 with the blocking thread 47 a rather thin or fine protrusion 177 may become subject to fracture or mechanical damage if the axial load applied were high.

Since a major part of the axial load will be directly transferred to the display member 160 via the radially outwardly directed deflection of the blocking element 174 and their axial abutment with the proximal abutment face 180 of the display member 160 the likelihood of mechanical damage to the protrusions 177 and the blocking elements 174 in response to excessive load can be reduced to a minimum.

From the enlarged illustrations according to FIGS. 15 and 16 it is also apparent that the protrusion 177 is located at a predefined axial distance d from the distal end of the blocking elements 174. In this way a kind of leverage effect can be obtained. Compared to the free end and the distal abutment face 176 the radially inwardly extending protrusion 177 is located at a reduced radial distance from an imaginary pivot or deflection axis of the flexible arm section 175. In this way and due to the rather elongated and straight shape of the blocking elements 174 and their flexible arm sections 175 a rather small radially outwardly directed deflection of the protrusions 177 leads to a rather large radial deflection at the distal end of the blocking elements 174. So in the blocking position B as shown in FIG. 16 the free end of the blocking element 174, in particular its distal abutment face 176 is located at a radial position that corresponds to the outer circumference of the sidewall 170 of the dose sleeve 72. The distal abutment face 176 may thus overlap to a rather large degree with the proximal abutment face 180 of the display member 160 to a rather large degree.

LIST OF REFERENCE NUMBERS 1 injection device
2 drive mechanism
4 distal direction
5 proximal direction
10 housing
11 cartridge holder
12 outer body
13 layer
14 window
15 aperture
16 thread
20 inner body
20a shaft
21 outer thread
22 spline
23 inner thread
24 stop
25 stop
30 piston rod
31 outer thread
32 outer thread
33 bearing
40 blocking structure
41 blocking segment
42 blocking segment
42b tangential end
43 blocking segment
43b tangential end
44 blocking segment
44a tangential end
45 blocking segment
45a tangential end
46 gap
46a gap
47 blocking thread
48 distal edge
49 proximal edge
50 last dose nut
51 external rib
52 inner thread
53 stop
70 dose member
71 dose dial/dose button
72 dose sleeve
73 arm
74 snap feature
80 cartridge
81 reservoir
82 bung
83 crimped metal cap
90 clutch sleeve
91 splines
92 teeth
93 aperture
94 splines
95 teeth 100 clicker
101 distal clicker
102 proximal clicker
103 clutch spring
104 splines
105 clicker teeth
106 clicker teeth
107 splines
108 splines
109 teeth
110 cartridge bias spring
120 cap
140 driver
141 distal drive sleeve
142 proximal drive sleeve
142*a* inner thread
143 coupler
144 thread
145 stop
146 teeth
147 teeth
148 flexible finger
149 hook
160 display member
161 number sleeve
162 dial sleeve
163 inner thread
164 stop
165 clutch feature
166 bearing face
167 stop
168 clicker
170 sidewall
171 recess
172 distal end
173 inside
174 blocking element
175 flexible arm section
176 abutment face
177 protrusion
178 beveled edge
178*a* proximal edge
179 radial gap
180 proximal abutment face
181 recess
182 radial gap

The invention claimed is:

1. A drive mechanism for an injection device for setting and dispensing a dose of a medicament, the drive mechanism comprising:
    an inner body fixable inside a housing of the injection device, the inner body comprising an elongated shaft extending in an axial direction, wherein the elongated shaft comprises an outer thread and a blocking structure on an outer circumference of the elongated shaft;
    a tube-shaped display member having an inner thread engaged with the outer thread of the inner body; and
    a dose member axially displaceable between a dose setting position and a dose dispensing position relative to the display member,
    wherein the dose member comprises at least one blocking element displaceable, pivotable, or bendable in a radial direction between a blocking position and a release position and engageable with the blocking structure for inducing a radial displacement of the at least one blocking element, and
    wherein when in the blocking position the at least one blocking element is engaged with the blocking structure and axially abuts with the display member to block an axial displacement of the dose member from the dose setting position towards the dose dispensing position.

2. The drive mechanism of claim 1, wherein the blocking structure comprises a blocking thread axially extending on the elongated shaft of the inner body, wherein the blocking thread and the outer thread have the same pitch.

3. The drive mechanism of claim 1, wherein the blocking structure comprises at least one spiral-shaped blocking segment separated in a tangential direction by at least one gap having a tangential size larger than or equal to a tangential size of the at least one blocking element.

4. The drive mechanism of claim 1, wherein the dose member comprises a dose sleeve at least partially enclosing the inner body, and wherein the at least one blocking element is arranged at an inside of the dose sleeve.

5. The drive mechanism of claim 4, wherein the at least one blocking element comprises a distal abutment face to axially abut with a proximal abutment face of the display member.

6. The drive mechanism of claim 4, wherein the at least one blocking element axially protrudes in a distal direction from a distal end of a side wall of the dose sleeve.

7. The drive mechanism of claim 4, wherein an inside of the dose sleeve comprises at least one recessed portion to receive the at least one blocking element when displaced, pivoted, or bended radially outwardly.

8. The drive mechanism of claim 4, wherein the dose member further comprises a dose dial axially fixed to the dose sleeve.

9. The drive mechanism of claim 4, wherein a proximal edge of the blocking structure comprises a beveled edge facing in a proximal direction to engage with a distal edge of the blocking structure.

10. The drive mechanism of claim 1, wherein the at least one blocking element comprises a flexible arm section extending in the axial direction and being flexible in the radial direction.

11. The drive mechanism of claim 1, wherein the at least one blocking element comprises at least one protrusion extending radially inwardly to engage with the blocking structure of the inner body.

12. The drive mechanism of claim 11, wherein the at least one protrusion comprises a beveled edge facing in a distal direction to engage with a proximal edge of the blocking structure.

13. The drive mechanism of claim 11, wherein the at least one protrusion is located at a predefined proximal distance from a distal abutment face of the at least one blocking element.

14. The drive mechanism of claim 1, further comprising a clutch between the dose member and the display member to:
    rotatably engage the dose member and the display member when the dose member is in the dose setting position; and
    rotatably release the dose member from the display member when the dose member is in the dose dispensing position.

15. The drive mechanism of claim 14, wherein an axial displacement of the dose member relative to the display member releases the clutch between the dose member and the display member.

16. The drive mechanism of claim 14, wherein when the at least one blocking element is engaged with the blocking structure and axially abuts with the display member, an axial displacement of the dose member relative to the display member that releases the clutch between the dose member and the display member is effectively prevented.

17. The drive mechanism of claim 1, further comprising a piston rod and a tube-shaped driver extending in the axial direction, wherein the piston rod comprises a first outer thread engaged with an inner thread of the inner body and comprises a second outer thread of opposite hand engaged with an inner thread of the driver.

18. An injection device for setting and dispensing of a dose of a medicament, comprising:
 a housing;
 a drive mechanism arranged inside the housing, the drive mechanism comprising:
  an inner body fixable inside the housing of the injection device, the inner body comprising an elongated shaft extending in an axial direction, wherein the elongated shaft comprises an outer thread and a blocking structure on an outer circumference of the elongated shaft,
  a tube-shaped display member having an inner thread engaged with the outer thread of the inner body, and
  a dose member axially displaceable between a dose setting position and a dose dispensing position relative to the display member,
  wherein the dose member comprises at least one blocking element displaceable, pivotable or bendable in a radial direction between a blocking position and a release position and engageable with the blocking structure for inducing a radial displacement of the at least one blocking element, and
  wherein when in the blocking position the at least one blocking element is engaged with the blocking structure and axially abuts with the display member to block an axial displacement of the dose member from the dose setting position towards the dose dispensing position; and
 a cartridge arranged inside the housing and filled with a liquid medicament.

19. The injection device of claim 18, wherein the blocking structure comprises a blocking thread axially extending on the elongated shaft of the inner body, wherein the blocking thread and the outer thread have the same pitch.

20. The injection device of claim 18, wherein the blocking structure comprises at least one spiral-shaped blocking segment separated in a tangential direction by at least one gap having a tangential size larger than or equal to a tangential size of the at least one blocking element.

* * * * *

UNITED STATES PATENT AND TRADEMARK OFFICE
CERTIFICATE OF CORRECTION

| | | |
|---|---|---|
| PATENT NO. | : 10,842,944 B2 | Page 1 of 1 |
| APPLICATION NO. | : 16/061624 | |
| DATED | : November 24, 2020 | |
| INVENTOR(S) | : James Alexander Senior | |

It is certified that error appears in the above-identified patent and that said Letters Patent is hereby corrected as shown below:

On the Title Page

Item [73], delete "Deustschland" and insert -- Deutschland --

Signed and Sealed this
First Day of October, 2024

Katherine Kelly Vidal
*Director of the United States Patent and Trademark Office*